United States Patent
Fujita et al.

(10) Patent No.: US 11,045,534 B2
(45) Date of Patent: Jun. 29, 2021

(54) IMMUNITY-INDUCING AGENT

(71) Applicant: TORAY INDUSTRIES, INC., Tokyo (JP)

(72) Inventors: Takayuki Fujita, Kamakura (JP); Fumiyoshi Okano, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 117 days.

(21) Appl. No.: 16/088,682

(22) PCT Filed: Mar. 27, 2017

(86) PCT No.: PCT/JP2017/012334
§ 371 (c)(1),
(2) Date: Sep. 26, 2018

(87) PCT Pub. No.: WO2017/170365
PCT Pub. Date: Oct. 5, 2017

(65) Prior Publication Data
US 2019/0091315 A1 Mar. 28, 2019

(30) Foreign Application Priority Data
Mar. 28, 2016 (JP) .............................. JP2016-064034

(51) Int. Cl.
| | |
|---|---|
| *A61K 39/395* | (2006.01) |
| *A61K 39/00* | (2006.01) |
| *C07K 14/54* | (2006.01) |
| *C07K 14/555* | (2006.01) |
| *C07K 14/705* | (2006.01) |
| *C12N 15/09* | (2006.01) |
| *A61K 31/7088* | (2006.01) |
| *A61K 38/00* | (2006.01) |
| *A61K 35/76* | (2015.01) |
| *A61K 38/21* | (2006.01) |
| *A61P 35/00* | (2006.01) |

(52) U.S. Cl.
CPC .. *A61K 39/001102* (2018.08); *A61K 31/7088* (2013.01); *A61K 35/76* (2013.01); *A61K 38/00* (2013.01); *A61K 38/21* (2013.01); *A61P 35/00* (2018.01); *C07K 14/54* (2013.01); *C07K 14/555* (2013.01); *C07K 14/705* (2013.01); *C12N 15/09* (2013.01); *A61K 2039/5158* (2013.01); *A61K 2039/53* (2013.01); *A61K 2039/572* (2013.01); *A61K 2039/804* (2018.08)

(58) Field of Classification Search
None
See application file for complete search history.

(56) References Cited

U.S. PATENT DOCUMENTS

| | | | | |
|---|---|---|---|---|
| 7,745,391 | B2 * | 6/2010 | Mintz | ................... A61P 31/00 |
| | | | | 514/19.3 |
| 9,416,192 | B2 * | 8/2016 | Okano | ................... A61P 11/00 |
| 10,493,137 | B2 * | 12/2019 | Ishibashi | .............. A61K 38/215 |
| 2005/0288487 | A1 | 12/2005 | Li et al. | |
| 2010/0278848 | A1 | 11/2010 | Berinstein et al. | |
| 2011/0130442 | A1 | 6/2011 | Kosaka et al. | |
| 2011/0229524 | A1 | 9/2011 | Fritsche et al. | |

FOREIGN PATENT DOCUMENTS

| | | |
|---|---|---|
| EA | 022743 B1 | 2/2016 |
| JP | 2003-513610 A | 4/2003 |
| JP | 2005-528087 A | 9/2005 |
| JP | 2012-110328 A | 6/2012 |
| JP | 2013-522276 A | 6/2013 |
| WO | WO 00/55180 A2 | 9/2000 |
| WO | WO 00/55320 A1 | 9/2000 |
| WO | WO 03/057252 A1 | 7/2003 |
| WO | WO 2011/113872 A1 | 9/2011 |
| WO | WO 2011/144718 A2 | 11/2011 |

OTHER PUBLICATIONS

Extended European Search Report dated Oct. 28, 2019, in European Patent Application No. 17774902.5.
International Search Report, issued in PCT/JP2017/012334, PCT/ISA/210, dated May 9, 2017.
Written Opinion of the International Searching Authority, issued in PCT/JP2017/012334, PCT/ISA/237, dated May 9, 2017.
Database, UniProtKB, Q9D8U6, Jan. 6, 2001 (Dec. 23, 2020); https://www.uniprot.org/uniprot/Q9D8U6.
Li et al., "Identification and expression of a new type II transmembrane protein in human mast cells," Genomics (2005), vol. 86, pp. 68-75.
Office Action dated Dec. 23, 2020, in Russian Patent Application No. 2018137802/10(062694).

\* cited by examiner

*Primary Examiner* — Yunsoo Kim
(74) *Attorney, Agent, or Firm* — Birch, Stewart, Kolasch & Birch, LLP

(57) ABSTRACT

The present application relates to a novel immunity-inducing agent for treatment and/or prevention of cancer. Specifically, the present application provides an immunity-inducing agent comprising, as an active ingredient, at least one polypeptide having immunity-inducing activity and selected from polypeptides derived from MCEMP1 and modified forms thereof, or a recombinant vector comprising a polynucleotide encoding the polypeptide and capable of expressing the polypeptide in vivo, and a method for inducing immunity, comprising administering the immunity-inducing agent to a subject.

7 Claims, 3 Drawing Sheets
Specification includes a Sequence Listing.

SEQUENCE LISTING

```
<160> NUMBER OF SEQ ID NOS: 20

<210> SEQ ID NO 1
<211> LENGTH: 1326
<212> TYPE: DNA
<213> ORGANISM: Homo sapiens
<220> FEATURE:
<221> NAME/KEY: CDS
<222> LOCATION: (26)..(589)

<400> SEQUENCE: 1
tggacaaatt tgcgggctgg ggacc atg gaa gtg gag gaa atc tac aag cac        52
                           Met Glu Val Glu Glu Ile Tyr Lys His
                           1               5 cag gaa gtc aag atg caa gca cca gcc ttc agg gac aag aaa cag ggg       100
Gln Glu Val Lys Met Gln Ala Pro Ala Phe Arg Asp Lys Lys Gln Gly
 10              15                  20                  25 gtc tca gcc aag aat caa ggt gcc cat gac cca gac tat gag aat atc       148
Val Ser Ala Lys Asn Gln Gly Ala His Asp Pro Asp Tyr Glu Asn Ile
                 30                  35                  40 acc ttg gcc ttc aaa aat cag gac cat gca aag ggt ggt cat tca cga       196
Thr Leu Ala Phe Lys Asn Gln Asp His Ala Lys Gly Gly His Ser Arg
             45                  50                  55 ccc acg agc caa gtc cca gcc cag tgc agg ccg ccc tca gac tcc acc       244
```

-continued

```
                Pro Thr Ser Gln Val Pro Ala Gln Cys Arg Pro Pro Ser Asp Ser Thr
                             60                  65                  70 cag gtc ccc tgc tgg ttg tac aga gcc atc ctg agc ctg tac atc ctc       292
Gln Val Pro Cys Trp Leu Tyr Arg Ala Ile Leu Ser Leu Tyr Ile Leu
         75                  80                  85 ctg gcc ctg gcc ttt gtc ctc tgc atc atc ctg tca gcc ttc atc atg       340
Leu Ala Leu Ala Phe Val Leu Cys Ile Ile Leu Ser Ala Phe Ile Met
 90                  95                 100                 105 gtg aag aat gct gag atg tcc aag gag ctg ctg ggc ttt aaa agg gag       388
Val Lys Asn Ala Glu Met Ser Lys Glu Leu Leu Gly Phe Lys Arg Glu
                    110                 115                 120 ctt tgg aat gtc tca aac tcc gta caa gca tgc gaa gag aga cag aag       436
Leu Trp Asn Val Ser Asn Ser Val Gln Ala Cys Glu Glu Arg Gln Lys
                125                 130                 135 aga ggc tgg gat tcc gtt cag cag agc atc acc atg gtc agg agc aag       484
Arg Gly Trp Asp Ser Val Gln Gln Ser Ile Thr Met Val Arg Ser Lys
            140                 145                 150 att gat aga tta gag acg aca tta gca ggc ata aaa aac att gac aca       532
Ile Asp Arg Leu Glu Thr Thr Leu Ala Gly Ile Lys Asn Ile Asp Thr
        155                 160                 165 aag gta cag aaa atc ttg gag gtg ctg cag aaa atg cca cag tcc tca       580
Lys Val Gln Lys Ile Leu Glu Val Leu Gln Lys Met Pro Gln Ser Ser
170                 175                 180                 185 cct caa taa atgagaggac attgtggcag ccaaagccac aacttggaag              629
Pro Gln atggggctgc acctgccaac gaagacggga aatgaccccc cccccccagc ctagtgtgaa     689 cctgccccte gtcccacgta tagaaaaacc tcgagtcatg gtgaatgagt gtctcggagt     749
tgctcgtgtg tgtgtacacc tgcgtgcgtg tgtgtgcgtg tgtgcgcgtg tgttcgtgta     809
tgtgcgtgtg tgcgtgcgcg tgtgtgtgca ttttgcaaag ggtggacatt tcagtgtatc     869
tcccagaaag gtgatgaatg aataggactg agagtcacag tgaatgtggc atgcatgcct     929
gtgtcatgtg acatatgtga gtctcggcat gtcacggtgg gtggctgtgt ctgagcacct     989
ccagcagatg tcactctgag tgtgggtgtt ggtgacatgc attgcacggg cctgtctccc    1049
tgtttgtgta acatactag agtatactgc ggcgtgtttt ctgtctaccc atgtcatggt     1109
gggggagatt tatctccgta catgtgggtg tcgccatgtg tgccctgtca ctatctgtgg    1169
ctgggtgaac ggctgtgtca ttatgagtgt gccgagttat gccaccctgt gtgctcaggg    1229
cacatgcaca cagacattta tctctgcact cacattttgt gacttatgaa gataaataaa    1289
gtcaagggaa aacagcgtca aaaaaaaaaa aaaaaaa                              1326
```

<210> SEQ ID NO 2
<211> LENGTH: 187
<212> TYPE: PRT
<213> ORGANISM: Homo sapiens

<400> SEQUENCE: 2

```
Met Glu Val Glu Glu Ile Tyr Lys His Gln Glu Val Lys Met Gln Ala
 1               5                  10                  15

Pro Ala Phe Arg Asp Lys Lys Gln Gly Val Ser Ala Lys Asn Gln Gly
                20                  25                  30

Ala His Asp Pro Asp Tyr Glu Asn Ile Thr Leu Ala Phe Lys Asn Gln
            35                  40                  45

Asp His Ala Lys Gly Gly His Ser Arg Pro Thr Ser Gln Val Pro Ala
        50                  55                  60

Gln Cys Arg Pro Pro Ser Asp Ser Thr Gln Val Pro Cys Trp Leu Tyr
```

```
            65                  70                  75                  80
Arg Ala Ile Leu Ser Leu Tyr Ile Leu Leu Ala Leu Ala Phe Val Leu
                    85                  90                  95

Cys Ile Ile Leu Ser Ala Phe Ile Met Val Lys Asn Ala Glu Met Ser
                    100                 105                 110

Lys Glu Leu Leu Gly Phe Lys Arg Glu Leu Trp Asn Val Ser Asn Ser
                    115                 120                 125

Val Gln Ala Cys Glu Glu Arg Gln Lys Arg Gly Trp Asp Ser Val Gln
            130                 135                 140

Gln Ser Ile Thr Met Val Arg Ser Lys Ile Asp Arg Leu Glu Thr Thr
145                 150                 155                 160

Leu Ala Gly Ile Lys Asn Ile Asp Thr Lys Val Gln Lys Ile Leu Glu
                    165                 170                 175

Val Leu Gln Lys Met Pro Gln Ser Pro Gln
                    180                 185

<210> SEQ ID NO 3
<211> LENGTH: 1124
<212> TYPE: DNA
<213> ORGANISM: Canis familiaris
<220> FEATURE:
<221> NAME/KEY: CDS
<222> LOCATION: (66)..(689)

<400> SEQUENCE: 3
ctcatctgcc atgacacctt ccggtgggtg gggatgtgtg tgggtaaact ggcccactgg      60 gaacc atg gag tct gag gaa atc tac acg aat cag aag gtc gag atg cag    110
      Met Glu Ser Glu Glu Ile Tyr Thr Asn Gln Lys Val Glu Met Gln
      1               5                   10                  15 gca gcc ttc aaa gac aag aaa cag agg gtc cca gct gat aag gaa ggt     158
Ala Ala Phe Lys Asp Lys Lys Gln Arg Val Pro Ala Asp Lys Glu Gly
                20                  25                  30 gca gat aac cct gac tat gag aat atc acc ttg gcc ttc aga aac cag     206
Ala Asp Asn Pro Asp Tyr Glu Asn Ile Thr Leu Ala Phe Arg Asn Gln
            35                  40                  45 gac cag cca aag ggc agc cat tta cca ccc aag aat cag agc aag cag     254
Asp Gln Pro Lys Gly Ser His Leu Pro Pro Lys Asn Gln Ser Lys Gln
        50                  55                  60 cca cct gcc agg aca cat cac acg gcc ttg gga ggg gcc cac gtc cca     302
Pro Pro Ala Arg Thr His His Thr Ala Leu Gly Gly Ala His Val Pro
    65                  70                  75 acc ctg tct agg ctg ccc tca gac tct ggc cag ctc ccc cgt tgt ctg     350
Thr Leu Ser Arg Leu Pro Ser Asp Ser Gly Gln Leu Pro Arg Cys Leu
80                  85                  90                  95 cac aga gtc atc atg agc ctg tac atg ctc ctc gcc ctg tcc tgc atc     398
His Arg Val Ile Met Ser Leu Tyr Met Leu Leu Ala Leu Ser Cys Ile
                    100                 105                 110 att ctc tta gtc ttg gtc ctc atg aag aat ctg gag atg tcc cag gag     446
Ile Leu Leu Val Leu Val Leu Met Lys Asn Leu Glu Met Ser Gln Glu
                115                 120                 125 ttg ctg gcc ctg aaa agg gag ctc tgg aat gtg tcc gtc tcg gtc caa     494
Leu Leu Ala Leu Lys Arg Glu Leu Trp Asn Val Ser Val Ser Val Gln
            130                 135                 140 gag tgc cag gag cag cag aat cag ggc tgg agc acc gtc cgg cag ctc     542
Glu Cys Gln Glu Gln Gln Asn Gln Gly Trp Ser Thr Val Arg Gln Leu
145                 150                 155 ctg gtg gag gcc aag cgt gac att tcc atg gtc ggg aga aat gcc cag     590
Leu Val Glu Ala Lys Arg Asp Ile Ser Met Val Gly Arg Asn Ala Gln
160                 165                 170                 175
```

```
ctt gcg agt gag aag gtg aag acg ctg aca gca gac ata agc cat atc      638
Leu Ala Ser Glu Lys Val Lys Thr Leu Thr Ala Asp Ile Ser His Ile
                180                 185                 190 aag agt aag tta cag gaa atc tcc aag atg ctg gag aag cca aag cca      686
Lys Ser Lys Leu Gln Glu Ile Ser Lys Met Leu Glu Lys Pro Lys Pro
            195                 200                 205 tag acctcaacat acgcgaggac atcgaagccc tggctgcagc ttggcggacg           739
gggctgcgcc tcccagtgaa gatggccacg tgtgtgcacc acgtgtgttg tgagcctaag   799
gcgtgacaca gtgggtggct gtgtcagcag ggaccacgaa agtgtgtcag cgtgttgttg   859
gcagcatgtg tagcaccgtg aacgcgtgtg actgtcctgt ggtatgttgt gtgtaaatgt   919
gtcacggcag agccgtggcg ggggcacccc acgtgtcact gtaattgtgg gtgccctgtc   979
actacctgtg ttggtgtgaa caggtgtctg ccaacgagcg actgaggatg tcacggaggg   1039
ggttcggagc atgtacacat gtatgtccat ttgttcccgc gctcacgttg tgtgatttgt   1099
gaagataaag gccgatggaa aagaa                                          1124
```

<210> SEQ ID NO 4
<211> LENGTH: 207
<212> TYPE: PRT
<213> ORGANISM: Canis familiaris

<400> SEQUENCE: 4

```
Met Glu Ser Glu Glu Ile Tyr Thr Asn Gln Lys Val Glu Met Gln Ala
1               5                   10                  15

Ala Phe Lys Asp Lys Lys Gln Arg Val Pro Ala Asp Lys Glu Gly Ala
            20                  25                  30

Asp Asn Pro Asp Tyr Glu Asn Ile Thr Leu Ala Phe Arg Asn Gln Asp
        35                  40                  45

Gln Pro Lys Gly Ser His Leu Pro Pro Lys Asn Gln Ser Lys Gln Pro
    50                  55                  60

Pro Ala Arg Thr His His Thr Ala Leu Gly Gly Ala His Val Pro Thr
65                  70                  75                  80

Leu Ser Arg Leu Pro Ser Asp Ser Gly Gln Leu Pro Arg Cys Leu His
                85                  90                  95

Arg Val Ile Met Ser Leu Tyr Met Leu Leu Ala Leu Ser Cys Ile Ile
            100                 105                 110

Leu Leu Val Leu Val Leu Met Lys Asn Leu Glu Met Ser Gln Glu Leu
        115                 120                 125

Leu Ala Leu Lys Arg Glu Leu Trp Asn Val Ser Val Ser Val Gln Glu
    130                 135                 140

Cys Gln Glu Gln Gln Asn Gln Gly Trp Ser Thr Val Arg Gln Leu Leu
145                 150                 155                 160

Val Glu Ala Lys Arg Asp Ile Ser Met Val Gly Arg Asn Ala Gln Leu
                165                 170                 175

Ala Ser Glu Lys Val Lys Thr Leu Thr Ala Asp Ile Ser His Ile Lys
            180                 185                 190

Ser Lys Leu Gln Glu Ile Ser Lys Met Leu Glu Lys Pro Lys Pro
        195                 200                 205
```

<210> SEQ ID NO 5
<211> LENGTH: 1416
<212> TYPE: DNA
<213> ORGANISM: Felis catus
<220> FEATURE:
<221> NAME/KEY: CDS

<222> LOCATION: (24)..(641)

<400> SEQUENCE: 5

```
tctgcttgaa tcaggaggtc agg atg caa gca gca gac ttc aaa ggc aag aaa        53
                          Met Gln Ala Ala Asp Phe Lys Gly Lys Lys
                            1               5                  10 cag agg gcc cca gac cat aag gaa ggt tcg gta cct caa ggt gca gac          101
Gln Arg Ala Pro Asp His Lys Glu Gly Ser Val Pro Gln Gly Ala Asp
             15                  20                  25 cct gac tat gag aat atc acc ttg acc ttc aga aac cag gag caa cca          149
Pro Asp Tyr Glu Asn Ile Thr Leu Thr Phe Arg Asn Gln Glu Gln Pro
         30                  35                  40 agg ggc agc cat tca cca ccc aag aat cga ggc aag cag cca cct gcc          197
Arg Gly Ser His Ser Pro Pro Lys Asn Arg Gly Lys Gln Pro Pro Ala
     45                  50                  55 agc ccg cac ctc aca gcc tcg gga ggg gcc cct gtc cca gcc tgg tcg          245
Ser Pro His Leu Thr Ala Ser Gly Gly Ala Pro Val Pro Ala Trp Ser
 60                  65                  70 aag cag gcc cca gac tct gcc cag gtc cct cgt tgg ctg cac aga gtc          293
Lys Gln Ala Pro Asp Ser Ala Gln Val Pro Arg Trp Leu His Arg Val
 75                  80                  85                  90 acc ctg agc ctg tac atc ctc ctt gcc ctg ttc tgc atc gtt ctc ttg          341
Thr Leu Ser Leu Tyr Ile Leu Leu Ala Leu Phe Cys Ile Val Leu Leu
                 95                 100                 105 gcc ttg gtc ctg gtg aag aat tct gag gtg tcc cag gag ctg ctg gtc          389
Ala Leu Val Leu Val Lys Asn Ser Glu Val Ser Gln Glu Leu Leu Val
             110                 115                 120 gtg aaa agg gag ctc cag aat gtc tcc atc tcg gga caa cag tgt cag          437
Val Lys Arg Glu Leu Gln Asn Val Ser Ile Ser Gly Gln Gln Cys Gln
         125                 130                 135 gag gag cag aaa cag ggc tgg agc agc gtc cag cag ctc atc acg gag          485
Glu Glu Gln Lys Gln Gly Trp Ser Ser Val Gln Gln Leu Ile Thr Glu
     140                 145                 150 gcc agg cag gac att gac atg atc aag aga aat gtc cac atc ggg aac          533
Ala Arg Gln Asp Ile Asp Met Ile Lys Arg Asn Val His Ile Gly Asn
155                 160                 165                 170 gag aaa gtg aag acg ctg tca aca gac tta agc caa atc aag act aaa          581
Glu Lys Val Lys Thr Leu Ser Thr Asp Leu Ser Gln Ile Lys Thr Lys
                 175                 180                 185 tta cat gaa atc tcc aag ata cta gag aag aag ccg cag cca cag ccc          629
Leu His Glu Ile Ser Lys Ile Leu Glu Lys Lys Pro Gln Pro Gln Pro
             190                 195                 200 aca gct caa taa atgagaagac attgacaccc aggctgcagc ttggaggacg              681
Thr Ala Gln
         205 gggctgcact tccccgtgaa gacggccgca tgtgtgcctc atggtgtcac gggagcgata        741 acacatgata cagtgggcgg ctgtgtcagc aaggaccgca gaagtgtgtc agcctgggcg        801 cgggtgttgg taacacgtgt tgcactgtga acacgtgtga atgtcctgtg gtatgttgtg        861 tgtgaatgtc atggagctgt gtgtgtgtgt gcgcgtgcgt gtgtgtgtgt ggagcacccc        921 ctacatcact gtaactgcgg gtgttgaggg tgtaccccgt cactccctgt gttgtgtgaa        981 caggtgggtg tcagtgtgtg actgattatg tcaccgaggg tgtgcagagc gggtacattt       1041 gtgcgttccc ttgtttctgc actcacgttt tgtgatttgt gacgataaag gccaatggga       1101 aagaatgtgg ctttcagatc tgttcctggg agcatctggg ggtgggggtg gggacccggt       1161 ggcggagggt ctgcaagtat taagggatga ggaaagtcac acagcaagca cgcggacgtg       1221 ataaccagga gccctggggg cacgagtgtg tgtgagcatg aatgccctga atgggtcctt       1281
```

```
ttgtgcccat gaacttgtac ccagcaagga acagtctccg tgtctgagac tgtgtgccca    1341
gcagggtttg tggcccgaga tatacactgt ttccctaagt ggggctcctg ggtggctcag    1401
tcggttaagc gtccg                                                     1416
```

<210> SEQ ID NO 6
<211> LENGTH: 205
<212> TYPE: PRT
<213> ORGANISM: Felis catus

<400> SEQUENCE: 6

```
Met Gln Ala Ala Asp Phe Lys Gly Lys Lys Gln Arg Ala Pro Asp His
1               5                   10                  15

Lys Glu Gly Ser Val Pro Gln Gly Ala Asp Pro Asp Tyr Glu Asn Ile
            20                  25                  30

Thr Leu Thr Phe Arg Asn Gln Glu Gln Pro Arg Gly Ser His Ser Pro
        35                  40                  45

Pro Lys Asn Arg Gly Lys Gln Pro Pro Ala Ser Pro His Leu Thr Ala
    50                  55                  60

Ser Gly Gly Ala Pro Val Pro Ala Trp Ser Lys Gln Ala Pro Asp Ser
65                  70                  75                  80

Ala Gln Val Pro Arg Trp Leu His Arg Val Thr Leu Ser Leu Tyr Ile
                85                  90                  95

Leu Leu Ala Leu Phe Cys Ile Val Leu Ala Leu Val Leu Val Lys
            100                 105                 110

Asn Ser Glu Val Ser Gln Glu Leu Leu Val Val Lys Arg Glu Leu Gln
        115                 120                 125

Asn Val Ser Ile Ser Gly Gln Gln Cys Gln Glu Glu Gln Lys Gln Gly
    130                 135                 140

Trp Ser Ser Val Gln Gln Leu Ile Thr Glu Ala Arg Gln Asp Ile Asp
145                 150                 155                 160

Met Ile Lys Arg Asn Val His Ile Gly Asn Glu Lys Val Lys Thr Leu
                165                 170                 175

Ser Thr Asp Leu Ser Gln Ile Lys Thr Lys Leu His Glu Ile Ser Lys
            180                 185                 190

Ile Leu Glu Lys Lys Pro Gln Pro Gln Pro Thr Ala Gln
        195                 200                 205
```

<210> SEQ ID NO 7
<211> LENGTH: 1132
<212> TYPE: DNA
<213> ORGANISM: Mus musculus
<220> FEATURE:
<221> NAME/KEY: CDS
<222> LOCATION: (21)..(572)

<400> SEQUENCE: 7

```
acgtgaatca accaagcaga atg cat gca tca gcc tcc cag gat aag aac cgg      53
                      Met His Ala Ser Ala Ser Gln Asp Lys Asn Arg
                      1               5                   10 agg aag cca ggt cat gat gaa ggt gct cac aat cct gac tac gag aat       101
Arg Lys Pro Gly His Asp Glu Gly Ala His Asn Pro Asp Tyr Glu Asn
            15                  20                  25 ata acc ttg gcc ttc aga aac aag gac caa ctc aaa ctc agc caa tca       149
Ile Thr Leu Ala Phe Arg Asn Lys Asp Gln Leu Lys Leu Ser Gln Ser
        30                  35                  40 aca ccc aca aaa caa gcc aag ttc aag aca tcc ctg gac cca gct gag       197
Thr Pro Thr Lys Gln Ala Lys Phe Lys Thr Ser Leu Asp Pro Ala Glu
```

|  |  |  |  |  |  |  |  |  |  |  |  |  |  |  |  |
|---|---|---|---|---|---|---|---|---|---|---|---|---|---|---|---|
|  |  |  | 45 |  |  |  | 50 |  |  |  | 55 |  |  |  |  |
| tcc | ccg | cct | tgg | ttg | tac | aga | acc | att | atg | atg | ttg | tat | gtt | ctc | ctt | 245 |
| Ser | Pro | Pro | Trp | Leu | Tyr | Arg | Thr | Ile | Met | Met | Leu | Tyr | Val | Leu | Leu |  |
| 60 |  |  |  | 65 |  |  |  | 70 |  |  |  | 75 |  |  |  |  |
| gct | ctc | gtc | ttt | tta | tcc | tgc | atc | gtc | ctc | tct | gct | ttg | gtc | ttg | gtg | 293 |
| Ala | Leu | Val | Phe | Leu | Ser | Cys | Ile | Val | Leu | Ser | Ala | Leu | Val | Leu | Val |  |
|  |  |  | 80 |  |  |  | 85 |  |  |  | 90 |  |  |  |  |  |
| aaa | aat | tct | gag | atg | tcc | aag | gag | ctg | tgg | acc | ttg | aaa | gca | gag | ctt | 341 |
| Lys | Asn | Ser | Glu | Met | Ser | Lys | Glu | Leu | Trp | Thr | Leu | Lys | Ala | Glu | Leu |  |
|  |  | 95 |  |  |  | 100 |  |  |  | 105 |  |  |  |  |  |  |
| tcg | aat | gtt | tca | gac | acg | gtg | tgg | aat | atc | cgg | gag | ctc | cag | aat | cag | 389 |
| Ser | Asn | Val | Ser | Asp | Thr | Val | Trp | Asn | Ile | Arg | Glu | Leu | Gln | Asn | Gln |  |
|  | 110 |  |  |  | 115 |  |  |  | 120 |  |  |  |  |  |  |  |
| caa | acg | agg | att | tgg | gaa | gct | gcc | cag | ggg | gac | atc | aag | gag | gtc | aag | 437 |
| Gln | Thr | Arg | Ile | Trp | Glu | Ala | Ala | Gln | Gly | Asp | Ile | Lys | Glu | Val | Lys |  |
| 125 |  |  |  | 130 |  |  |  | 135 |  |  |  |  |  |  |  |  |
| aag | acc | ctt | ggc | aca | gtc | atg | agt | agc | atc | cag | act | gga | aac | gac | cgg | 485 |
| Lys | Thr | Leu | Gly | Thr | Val | Met | Ser | Ser | Ile | Gln | Thr | Gly | Asn | Asp | Arg |  |
| 140 |  |  |  | 145 |  |  |  | 150 |  |  |  | 155 |  |  |  |  |
| ctg | aag | act | gtg | ccg | gca | gat | ata | acc | caa | atc | aag | aaa | act | ctt | gag | 533 |
| Leu | Lys | Thr | Val | Pro | Ala | Asp | Ile | Thr | Gln | Ile | Lys | Lys | Thr | Leu | Glu |  |
|  |  |  | 160 |  |  |  | 165 |  |  |  | 170 |  |  |  |  |  |
| gcg | cta | gaa | aag | aag | gca | cag | cct | cag | ccc | agt | aca | taa | gaggacacca |  |  | 582 |
| Ala | Leu | Glu | Lys | Lys | Ala | Gln | Pro | Gln | Pro | Ser | Thr |  |  |  |  |  |
|  |  |  | 175 |  |  |  | 180 |  |  |  |  |  |  |  |  |  |

```
cagcagtacc tgtgaagact ccgaattgca cctgctagtg aagatggcag atgggggtgg    642
gtactgagct tgagtgtgaa cctgccgtgc atcctcatat aaaaaagatt ctccaccagg    702
gggaatgagt gttgaagagg tgtgtatgca aatgagcatt tggggtttcc atgtattcca    762
ggagaagggt ttatggtgga aagagaacat ggcagtcaca gcaggtgtta ctctttatgg    822
gccacatagg tgtatgccct ggcttatgtg agtataggca tgtcctggtt ggcagctatt    882
cccgagaagt ccccaaagtg taagtgacat gtaggcacatg cctccccatt ctcttgctca    942
tgtatgtgca tctggctgtt ctgtatgtgt gtcactgaag tggtgggtga tagacatcac   1002
cctggagatg tgtcatggca tgggtcattc ctagtgtttt tggtcatgtc agcttgtgtg   1062
ttcagggcat gcacacaaat gtagccatcg atttctgcac ttgtatttat gattcaagaa   1122
gataaatgcc                                                          1132
```

<210> SEQ ID NO 8
<211> LENGTH: 183
<212> TYPE: PRT
<213> ORGANISM: Mus musculus

<400> SEQUENCE: 8

| Met | His | Ala | Ser | Ala | Ser | Gln | Asp | Lys | Asn | Arg | Arg | Lys | Pro | Gly | His |
|---|---|---|---|---|---|---|---|---|---|---|---|---|---|---|---|
| 1 |  |  |  | 5 |  |  |  |  | 10 |  |  |  |  | 15 |  |

| Asp | Glu | Gly | Ala | His | Asn | Pro | Asp | Tyr | Glu | Asn | Ile | Thr | Leu | Ala | Phe |
|---|---|---|---|---|---|---|---|---|---|---|---|---|---|---|---|
|  |  |  | 20 |  |  |  |  | 25 |  |  |  |  | 30 |  |  |

| Arg | Asn | Lys | Asp | Gln | Leu | Lys | Leu | Ser | Gln | Ser | Thr | Pro | Thr | Lys | Gln |
|---|---|---|---|---|---|---|---|---|---|---|---|---|---|---|---|
|  |  | 35 |  |  |  |  | 40 |  |  |  |  | 45 |  |  |  |

| Ala | Lys | Phe | Lys | Thr | Ser | Leu | Asp | Pro | Ala | Glu | Ser | Pro | Pro | Trp | Leu |
|---|---|---|---|---|---|---|---|---|---|---|---|---|---|---|---|
|  | 50 |  |  |  |  | 55 |  |  |  |  | 60 |  |  |  |  |

| Tyr | Arg | Thr | Ile | Met | Met | Leu | Tyr | Val | Leu | Leu | Ala | Leu | Val | Phe | Leu |
|---|---|---|---|---|---|---|---|---|---|---|---|---|---|---|---|
| 65 |  |  |  |  | 70 |  |  |  |  | 75 |  |  |  |  | 80 |

| Ser | Cys | Ile | Val | Leu | Ser | Ala | Leu | Val | Leu | Val | Lys | Asn | Ser | Glu | Met |
|---|---|---|---|---|---|---|---|---|---|---|---|---|---|---|---|
|  |  |  |  | 85 |  |  |  |  | 90 |  |  |  |  | 95 |  |

```
Ser Lys Glu Leu Trp Thr Leu Lys Ala Glu Leu Ser Asn Val Ser Asp
        100                 105                 110
Thr Val Trp Asn Ile Arg Glu Leu Gln Asn Gln Gln Thr Arg Ile Trp
            115                 120                 125
Glu Ala Ala Gln Gly Asp Ile Lys Glu Val Lys Lys Thr Leu Gly Thr
        130                 135                 140
Val Met Ser Ser Ile Gln Thr Gly Asn Asp Arg Leu Lys Thr Val Pro
145                 150                 155                 160
Ala Asp Ile Thr Gln Ile Lys Lys Thr Leu Glu Ala Leu Glu Lys Lys
                165                 170                 175
Ala Gln Pro Gln Pro Ser Thr
            180
```

<210> SEQ ID NO 9
<211> LENGTH: 20
<212> TYPE: DNA
<213> ORGANISM: Artificial
<220> FEATURE:
<223> OTHER INFORMATION: T3 primer

<400> SEQUENCE: 9
aattaaccct cactaaaggg                                              20

<210> SEQ ID NO 10
<211> LENGTH: 19
<212> TYPE: DNA
<213> ORGANISM: Artificial
<220> FEATURE:
<223> OTHER INFORMATION: T7 primer

<400> SEQUENCE: 10
taatacgact cactatagg                                               19

<210> SEQ ID NO 11
<211> LENGTH: 20
<212> TYPE: DNA
<213> ORGANISM: Artificial
<220> FEATURE:
<223> OTHER INFORMATION: canis RT primer sense

<400> SEQUENCE: 11
ccacgtccca accctgtcta                                              20

<210> SEQ ID NO 12
<211> LENGTH: 20
<212> TYPE: DNA
<213> ORGANISM: Artificial
<220> FEATURE:
<223> OTHER INFORMATION: canis RT primer antisense

<400> SEQUENCE: 12
gtgctccagc cctgattctg                                              20

<210> SEQ ID NO 13
<211> LENGTH: 20
<212> TYPE: DNA
<213> ORGANISM: Artificial
<220> FEATURE:
<223> OTHER INFORMATION: human RT primer sense

<400> SEQUENCE: 13
tggccttcaa aaatcaggac                                              20

```
<210> SEQ ID NO 14
<211> LENGTH: 21
<212> TYPE: DNA
<213> ORGANISM: Artificial
<220> FEATURE:
<223> OTHER INFORMATION: human RT primer antisense

<400> SEQUENCE: 14
aggctcagga tggctctgta c                                            21

<210> SEQ ID NO 15
<211> LENGTH: 20
<212> TYPE: DNA
<213> ORGANISM: Artificial
<220> FEATURE:
<223> OTHER INFORMATION: mouse RT primer sense

<400> SEQUENCE: 15
tccaaggagc tgtggacctt                                              20

<210> SEQ ID NO 16
<211> LENGTH: 20
<212> TYPE: DNA
<213> ORGANISM: Artificial
<220> FEATURE:
<223> OTHER INFORMATION: mouse RT primer antisense

<400> SEQUENCE: 16
agtcttcagc cggtcgtttc                                              20

<210> SEQ ID NO 17
<211> LENGTH: 37
<212> TYPE: DNA
<213> ORGANISM: Artificial
<220> FEATURE:
<223> OTHER INFORMATION: mouse mcemp1 EcoRI primer sense

<400> SEQUENCE: 17
gaattcgccg ccaccatgca tgcatcagcc tcccagg                           37

<210> SEQ ID NO 18
<211> LENGTH: 29
<212> TYPE: DNA
<213> ORGANISM: Artificial
<220> FEATURE:
<223> OTHER INFORMATION: mouse mcemp1 NotI primer antisense

<400> SEQUENCE: 18
gcggccgctt atgtactggg ctgaggctg                                    29

<210> SEQ ID NO 19
<211> LENGTH: 39
<212> TYPE: DNA
<213> ORGANISM: Artificial
<220> FEATURE:
<223> OTHER INFORMATION: human MCEMP1 EcoRI primer sense

<400> SEQUENCE: 19
gaattcgccg ccaccatgga agtggaggaa atctacaag                         39

<210> SEQ ID NO 20
<211> LENGTH: 29
<212> TYPE: DNA
<213> ORGANISM: Artificial
<220> FEATURE:
<223> OTHER INFORMATION: human MCEMP1 NotI primer antisense
```

```
<400> SEQUENCE: 20
gcggccgctt attgaggtga ggactgtgg                                29
```

IMMUNITY-INDUCING AGENT

TECHNICAL FIELD

The present invention relates to a novel immunity-inducing agent that is useful as a therapeutic and/or preventive agent for cancers, or the like.

BACKGROUND ART

Cancer is the overall leading cause of death. At present, the primary form of cancer treatment technique is surgical treatment, which is carried out in combination with radiation treatment and chemotherapy. In spite of the development of novel surgical techniques and the discovery of novel anti-cancer agents of recent years, outcomes from cancer treatment still remain unimproved, except in the cases of some types of cancers. In recent years, for example, cancer antigens recognized by cytotoxic T cells that are reactive to cancer and genes encoding cancer antigens have been identified along with the development of molecular biology and cancer immunology, and expectations for antigen-specific immunotherapy have increased.

It has been reported that Mast Cell-Expressed Membrane Protein 1 (MCEMP1), a type 2 transmembrane protein, is expressed on the cell membrane in a manner specific for mast cells, suggesting the possibility that the protein participates in mast cell differentiation, immune response, and allergic response (Non Patent Literature 1). However, there have been no reports that the MCEMP1 protein has an immunity-inducing activity against cancer cells and thus is useful for treating and preventing cancers.

PRIOR ART LITERATURE

Non Patent Literature

Non Patent Literature 1: Kang Li. et al. Genomics, 86:68-75(2005)

SUMMARY OF INVENTION

Problem to be Solved by the Invention

It is an object of the present invention to find a novel polypeptide useful for a therapeutic and/or preventive agent for cancer and to provide use of such polypeptide as an immunity-inducing agent.

Means for Solution of Problem

The present inventors conducted intensive studies, and as a result, have now obtained a cDNA encoding a protein binding to an antibody present in sera from cancer-bearing living bodies by the SEREX method using a cDNA library derived from the canine testis along with sera of dogs with leukemia. Based on the cDNA, the present inventors prepared a polypeptide of canine Mast Cell-Expressed Membrane Protein 1 (hereinafter referred to as MCEMP1) having the amino acid sequence represented by SEQ ID NO: 4. Furthermore, based on human, cat and mouse homologous genes to the obtained canine gene, the present inventors prepared human, cat and mouse MCEMP1 polypeptides having the amino acid sequences represented by SEQ ID NOs: 2, 6, and 8. The present inventors have now found that these MCEMP1 polypeptides are specifically expressed in leukemia, myelodysplastic syndrome, osteosarcoma, thymoma, mastocytoma, and perianal adenocarcinoma. Furthermore, they have now further found that immune cells against MCEMP1 can be induced in vivo by administering these MCEMP1 to living bodies, and that the size of a tumor in the living bodies where MCEMP1 is expressed can be reduced. Moreover, the present inventors have now found that a recombinant vector capable of expressing a polynucleotide encoding MCEMP1 polypeptide or a fragment thereof induces an antitumor effect on an MCEMP1 expressing cancer in vivo.

The present inventors have now also found that the MCEMP1 polypeptide is presented by an antigen-presenting cell and has an ability (also referred to as "immunity-inducing activity") to activate and proliferate a cytotoxic T cell specific to the polypeptide; that the polypeptide is useful for treating and/or preventing cancers because of the ability; and that the antigen-presenting cell, which was in contact with the polypeptide, and the T cell, which was in contact with the antigen-presenting cell, are useful for treating and/or preventing cancers. Based on the findings, the present invention was accomplished.

Accordingly, the present invention includes the following features (1) to (11):

(1) An immunity-inducing agent comprising, as an active ingredient, at least one polypeptide having immunity-inducing activity and selected from any of the following polypeptides (a) to (d), or a recombinant vector comprising a polynucleotide encoding the polypeptide and capable of expressing said polypeptide in vivo:

(a) a polypeptide consisting of 7 or more consecutive amino acids or a full-length sequence in the amino acid sequence represented by SEQ ID NO: 2, 4, 6, or 8 in the Sequence Listing;

(b) a polypeptide consisting of an amino acid sequence obtained by deletion, substitution or addition of one or several amino acids in the amino acid sequence represented by SEQ ID NO: 2, 4, 6, or 8 in the Sequence Listing;

(c) a polypeptide consisting of an amino acid sequence having a sequence identity of 90% or more with the amino acid sequence represented by SEQ ID NO: 2, 4, 6, or 8 in the Sequence Listing;

(d) a polypeptide comprising any of the polypeptides (a) to (c) as a partial sequence.

(2) The immunity-inducing agent according to (1), which is an agent for treating antigen-presenting cells.

(3) The immunity-inducing agent according to (1), which is an active ingredient for a therapeutic and/or preventing agent for cancer.

(4) The immunity-inducing agent according to (3), wherein the cancer is an MCEMP1 expressing cancer.

(5) The immunity-inducing agent according to (3) or (4), wherein the cancer is leukemia, myelodysplastic syndrome, osteosarcoma, thymoma, mastocytoma or perianal adenocarcinoma.

(6) The immunity-inducing agent according to any one of (1) to (5), further comprising an immunoenhancer.

(7) The immunity-inducing agent according to (6), wherein the immunoenhancer is at least one selected from the group consisting of Freund's incomplete adjuvant, Montanide, Poly IC and derivatives thereof, CpG oligonucleotides, interleukin 12, interleukin 18, interferon $\alpha$, interferon $\beta$, interferon $\omega$, interferon $\gamma$, and Flt 3 ligand.

(8) A method for preparing an antigen-presenting cell containing a complex of the polypeptide defined in (1) and an MHC molecule, comprising contacting the polypeptide with an antigen-presenting cell from a subject ex vivo or in vitro.

(9) The method according to (8), wherein the antigen-presenting cell is a dendritic cell or B cell having an MHC class I molecule.

(10) A method for preparing a cytotoxic T cell specific to the polypeptide defined in (1), comprising contacting the antigen-presenting cell obtained by the method according to (8) or (9) with a T cell from a subject ex vivo or in vitro, thereby activating the T cell.

(11) A method for inducing immunity, comprising administering, to a subject, at least one polypeptide having immunity-inducing activity and selected from the following polypeptides (a) to (d), or a recombinant vector comprising a polynucleotide encoding the polypeptide and capable of expressing said polypeptide in vivo:

(a) a polypeptide consisting of 7 or more consecutive amino acids or a full-length sequence in the amino acid sequence represented by SEQ ID NO: 2, 4, 6, or 8 in the Sequence Listing;

(b) a polypeptide consisting of an amino acid sequence obtained by deletion, substitution or addition of one or several amino acids in the amino acid sequence represented by SEQ ID NO: 2, 4, 6, or 8 in the Sequence Listing;

(c) a polypeptide consisting of an amino acid sequence having a sequence identity of 90% or more with the amino acid sequence represented by SEQ ID NO: 2, 4, 6, or 8 in the Sequence Listing;

(d) a polypeptide comprising any of the polypeptides (a) to (c) as a partial sequence.

According to the present invention, there is provided a novel immunity-inducing agent useful for treatment and/or prevention of cancers, and the like. When the polypeptide used in the invention is administered to a subject, immune cells can be induced in the living body and a cancer which has already occurred can be reduced in size or regressed, as specifically shown in Examples described later. Thus, the polypeptide is useful for treating and preventing cancers.

The description includes the contents disclosed in JP Patent Application No. 2016-064034 to which the present application claims the priority.

MODE FOR CARRYING OUT THE INVENTION

Figure 1:
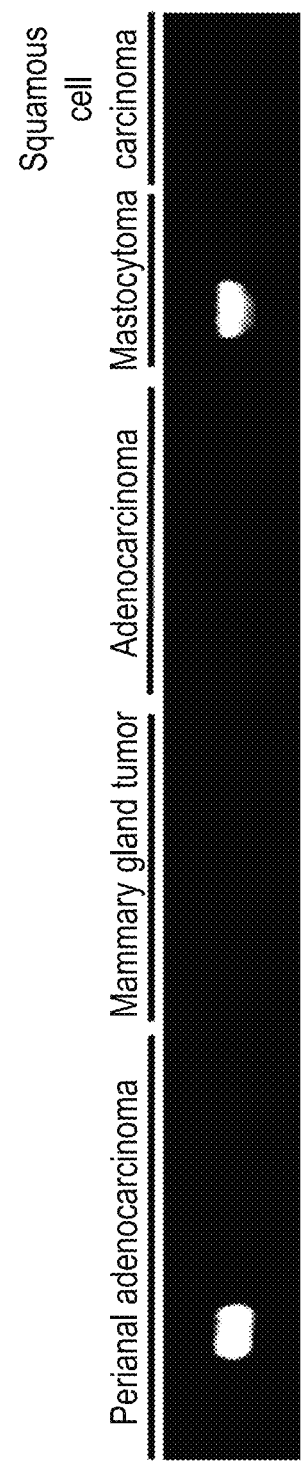
FIG. 1 This figure shows expression patterns of the identified MCEMP1 gene in canine tumor tissues. Reference number 1 shows expression patterns of the canine MCEMP1 gene in individual canine tumor tissues.

The present invention will be more specifically described.
1. Polypeptide

As a polypeptide contained as an active ingredient in the immunity-inducing agent of the present invention, polypeptides defined in the following (a) to (d) are included. Herein, the term "polypeptide" refers to a molecule formed of a plurality of amino acids which are bound via peptide linkage, and includes not only a polypeptide molecule constituted of a large number of amino acids but also a low molecular-weight molecule (i.e., an oligopeptide) constituted of a small number of amino acids, or a full-length protein.

(a) A polypeptide consisting of 7 or more consecutive amino acids or a full-length sequence in a polypeptide having the amino acid sequence represented by SEQ ID NO: 2, 4, 6, or 8 in the Sequence Listing, and having immunity-inducing activity.

(b) a polypeptide consisting of an amino acid sequence obtained by deletion, substitution or addition of one or several amino acids in the amino acid sequence represented by SEQ ID NO: 2, 4, 6, or 8 in the Sequence Listing, and having immunity-inducing activity.

(c) a polypeptide consisting of an amino acid sequence having a sequence identity of 90% or more with the amino acid sequence represented by SEQ ID NO: 2, 4, 6, or 8 in the Sequence Listing, and having immunity-inducing activity.

(d) a polypeptide comprising any of the polypeptides (a) to (c) as a partial sequence, and having immunity-inducing activity.

In the present invention, the phrase "having an(the) amino acid sequence" means that amino acid residues align in the order shown in the sequence. Accordingly, for example, the "polypeptide having the amino acid sequence represented by SEQ ID NO: 8" refers to a polypeptide having a size of 183 amino acid residues and consisting of the amino acid sequence of Met, His, Ala, Ser, Ala . . . (omission) . . . Gln, Pro, Ser, and Thr represented by SEQ ID NO: 8. The "polypeptide having the amino acid sequence represented by SEQ ID NO: 8" is sometimes simply referred to as, for example, "the polypeptide of SEQ ID NO: 8". The same is applied to the expression "having a(the) nucleotide sequence". In the phrase, the term "having" may be replaced by the term "consisting of".

Here, the term "immunity-inducing activity" refers to an ability to induce immune cells secreting cytokines such as interferon in the living body.

Whether or not the polypeptide above has an immunity-inducing activity can be confirmed by using, for example, ELISpot Assay known in the art. More specifically, the immunity-inducing activity can be evaluated by: obtaining cells like peripheral blood mononuclear cells from a living body to which the polypeptide to be evaluated for immunity-inducing activity has been administered; co-culturing the cells with the polypeptide; and measuring the amount of a cytokine produced from the cells by using a specific antibody, thereby determining the number of immune cells in the cells.

As described in Examples below, when the recombinant polypeptides of the above (a) to (d) each are administered to cancer-bearing living bodies, tumors can also be regressed due to the immunity-inducing activity of the polypeptides. Accordingly, the immunity-inducing activity can be evaluated as an ability to suppress proliferation of cancer cells or reduce the size of a cancer tissue (tumor) or eliminate a cancer tissue (tumor) (hereinafter referred to as "antitumor activity"). The antitumor activity of a polypeptide can be confirmed by actually administering the polypeptide to cancer-bearing living bodies and examining, for example, whether or not a tumor is reduced in size, for example, as specifically described in Examples below. Alternatively, the antitumor activity of a polypeptide may be evaluated by examining, for example, whether a cytotoxic T cell, which is induced by administering the polypeptide to cancer-bearing living bodies, exhibits cytotoxic activity to a tumor. The cytotoxic activity of a T cell can be determined in vivo by administering an antibody, which removes the T cell from a living body, and examining whether or not a tumor is thereby increased in size. However, the method of determining cytotoxic activity is not limited to those mentioned above.

Alternatively, the antitumor activity of the polypeptides may be evaluated by examining whether or not T cells stimulated with the polypeptides (more specifically, T cells contacted with antigen-presenting cells that present the polypeptides) exhibit cytotoxic activity against tumor cells in vitro. The T cells and the antigen-presenting cells may be contacted with each other by co-culturing both cells in a liquid medium, as described later. The cytotoxic activity may be measured by the known method called $^{51}$Cr release assay, for example, described in Int. J. Cancer, 58: p. 317, 1994. When the above-mentioned polypeptides are used for treatment and/or prevention of cancers, the immunity-inducing activity is preferably evaluated by using the antitumor activity as an indicator although such evaluation is not particularly limited thereto.

In the present invention, the amino acid sequences represented by SEQ ID NOs: 2, 4, 6, and 8, respectively, as described in the Sequence Listing are the amino acid sequences of MCEMP1, which were isolated, as the polypeptides that bind to antibodies specifically present in the sera derived from cancer-bearing dogs, by the SEREX method using a cDNA library derived from canine testis and the sera of cancer-bearing dogs, and as homologs from human, cat, and mouse (see, Example 1). Human MCEMP1, which is a human homolog homologous with dog MCEMP1, has a nucleotide sequence identity of 70% and an amino acid sequence identity of 51%. Cat MCEMP1, which is a cat homolog, has a nucleotide sequence identity of 83% and an amino acid sequence identity of 64%. Mouse MCEMP1, which is a mouse homolog, has a nucleotide sequence identity of 65% and an amino acid sequence identity of 47%.

The polypeptide defined in the (a) above is a polypeptide which consists of 7 or more consecutive amino acids, preferably 8, 9 or 10 or more consecutive amino acids in the polypeptide having the amino acid sequence represented by SEQ ID NO: 2, 4, 6, or 8, and which has an immunity-inducing activity. Particularly preferably, the polypeptide has the amino acid sequence represented by SEQ ID NO: 2, 4, 6, or 8. As known in the art, if a polypeptide has approximately 7 or more amino acid residues, then the polypeptide can exhibit antigenicity and immunogenicity. As such, where the polypeptide consists of 7 or more consecutive amino acid residues or all amino acid residues (full-length sequence) in the amino acid sequence represented by SEQ ID NO: 2, 4, 6, or 8, it can possess an immunity-inducing activity and thus can be used for preparation of the immunity-inducing agent of the present invention.

As the principle of immune induction by administration of a cancer antigenic polypeptide, the following process is known: a polypeptide is incorporated into an antigen-presenting cell and then degraded into smaller fragments by peptidases in the cell, followed by presentation of the fragments on the surface of the cell. The fragments are then recognized by a cytotoxic T cell or the like, which selectively kills cells presenting the antigen. The size of the polypeptide presented on the surface of the antigen-presenting cell is relatively small and is approximately 7 to 30 amino acids. Therefore, from the viewpoint of presenting the polypeptide on the surface of the antigen-presenting cell, one preferred embodiment of the above-described polypeptide (a) is a polypeptide composed of approximately 7 to 30 consecutive amino acids in the amino acid sequence represented by SEQ ID NO: 2, 4, 6, or 8, and more preferably, a polypeptide composed of approximately 8 to 30 or approximately 9 to 30 amino acids is sufficient as the polypeptide (a). In some cases, these relatively small polypeptides are presented directly on the surface of the antigen-presenting cell without being incorporated into the antigen-presenting cells.

Further, since a polypeptide incorporated into an antigen-presenting cell is cleaved at random sites by peptidases in the cell to yield various polypeptide fragments, which are then presented on the surface of the antigen-presenting cell, administration of a large polypeptide such as the full-length region of SEQ ID NO: 2, 4, 6, or 8 inevitably causes production of polypeptide fragments by degradation in the antigen-presenting cell, which fragments are effective for immune induction via the antigen-presenting cell. Therefore, also for immune induction via antigen-presenting cells, a large polypeptide can be preferably used, and the polypeptide may be composed of not less than 30, preferably not less than 100, more preferably not less than 200 amino acids. The polypeptide may be still more preferably composed of the full-length region of SEQ ID NO: 2, 4, 6, or 8.

The polypeptide described in the (c) above is a polypeptide which is obtained by substitution, deletion and/or insertion of a small number of (preferably one or several) amino acid residues in the polypeptide described in the (a) above, which has a sequence identity of 90% or more, preferably 95% or more, more preferably 98% or more, still more preferably 99% or more, or 99.5% or more with the original sequence, and which has immunity-inducing activity. Generally, it is widely known to those skilled in the art that a protein antigen, even if it has a substitution, deletion, or insertion of a small number of amino acid residues in the amino acid sequence of the protein, may have substantially the same antigenicity as the original protein. Accordingly, a polypeptide defined in the above (c) can exhibit immunity-inducing activity, and thus, can be used in preparation of the immunity-inducing agent of the present invention. It is also preferable that the polypeptide of the above (b) is a polypeptide obtained by substitution, deletion, and/or insertion of one to several amino acid residues in the amino acid sequence represented by SEQ ID NO: 2, 4, 6, or 8. Herein, the term "several" refers to an integer of 2 to 10, preferably 2 to 6 and further preferably 2 to 4.

Here, the term "sequence identity" of amino acid sequences or nucleotide sequences means the value calculated by aligning two amino acid sequences (or nucleotide sequences) to be compared such that the number of matched amino acid residues (or nucleotides) is as the largest as possible between the amino acid sequences (or nucleotide sequences), and dividing the number of matched amino acid residues (or the number of matched nucleotides) by the total number of amino acid residues (or the total number of nucleotides), which value is represented as a percentage. When the alignment is carried out, a gap(s) is/are inserted into one or both of the two sequences to be compared as required. Such alignment of sequences can be carried out using a well-known program such as BLAST, FASTA or CLUSTAL W. When a gap(s) is/are inserted, the above-described total number of amino acid residues is the number of residues calculated by counting one gap as one amino acid residue. When the thus counted total number of amino acid residues is different between the two sequences to be compared, the sequence identity (%) is calculated by dividing the number of matched amino acid residues by the total number of amino acid residues in the longer sequence.

The 20 types of amino acids constituting naturally occurring proteins may be classified into groups in each of which similar properties are shared, for example, into neutral amino acids with side chains having low polarity (Gly, Ile, Val, Leu, Ala, Met, Pro), neutral amino acids having hydrophilic side chains (Asn, Gln, Thr, Ser, Tyr, Cys), acidic amino acids (Asp, Glu), basic amino acids (Arg, Lys, His), and aromatic amino acids (Phe, Tyr, Trp). It is known that, in most cases, substitutions of amino acids within the same group do not change the properties of the polypeptide. Therefore, in cases where an amino acid residue(s) in the polypeptide (a) of the present invention is/are substituted, the probability that the immunity-inducing activity can be maintained becomes high by substitution between amino acid residues within each group, and so the substitution is preferred.

The polypeptide (d) comprises any of the polypeptides (a) to (c) as a partial sequence and has an immunity-inducing activity. That is, the polypeptide (a) or (b) has another amino acid or polypeptide added at one end or both ends of any of the polypeptides (a) to (c), and has an immunity-inducing activity. Such a polypeptide can also be used in preparation of the immunity-inducing agent of the present invention.

The above-described polypeptides can be synthesized by, for example, a chemical synthesis method such as the Fmoc method (fluorenylmethyloxycarbonyl method) or the tBoc method (t-butyloxycarbonyl method). Further, they can be synthesized by conventional methods using various types of commercially available peptide synthesizers. Further, the polypeptide of interest can be obtained using known genetic engineering techniques, by preparing a polynucleotide encoding the above polypeptide and incorporating the polynucleotide into an expression vector, which is then introduced into a host cell, followed by allowing the polypeptide to be produced in the host cell.

The polynucleotide encoding the above polypeptide can be easily prepared by a known genetic engineering technique or a conventional method using a commercially available nucleic acid synthesizer. For example, DNA having the nucleotide sequence shown in SEQ ID NO: 3 can be prepared by carrying out PCR using a canine chromosomal DNA or cDNA library as a template, and a pair of primers designed such that the nucleotide sequence shown in SEQ ID NO: 3 can be amplified using the primers. DNA having the nucleotide sequence of SEQ ID NO: 1 can be similarly prepared by using a human chromosomal DNA or cDNA library as the template. The reaction conditions for the PCR can be set appropriately, and examples thereof include, but are not limited to, repeating the reaction process of 94° C. for 30 seconds (denaturation), 55° C. for 30 seconds to 1 minute (annealing) and 72° C. for 1 minute (extension) as one cycle, for 30 cycles for example, followed by the reaction at 72° C. for 7 minutes. Further, the desired DNA can be isolated by preparing an appropriate probe(s) or primer(s) based on the information of the nucleotide sequences and the amino acid sequences shown in SEQ ID NO: 1 and 3 in Sequence Listing described herein, and screening a cDNA library of human, dog or the like using the probe(s) or primer(s). The cDNA library is preferably prepared from cells, organs or tissues expressing the protein of SEQ ID NO: 2 or 4. The above-described operations such as preparation of a probe(s) or primer(s), construction of a cDNA library, screening of a cDNA library and cloning of a gene of interest are known to those skilled in the art, and can be carried out according to the methods described in Molecular Cloning, Second Edition; Current Protocols in Molecular Biology; and/or the like. From the thus obtained DNA, DNA encoding the polypeptide (a) can be obtained. Further, since the codons encoding each amino acid are known, the nucleotide sequence of a polynucleotide encoding a specific amino acid sequence can be easily specified. Therefore, since the nucleotide sequence of a polynucleotide encoding the polypeptide (b) to (d) can also be easily specified, such a polynucleotide can also be easily synthesized using a commercially available nucleic acid synthesizer according to a conventional method.

The host cells are not restricted as long as they can express the above-described polypeptide, and examples thereof include, but are not limited to, prokaryotic cells such as $E.\ coli$; and eukaryotic cells such as cultured mammalian cells including monkey kidney cells COS1 and Chinese hamster ovary cells CHO; budding yeast; fission yeast; silkworm cells; and $Xenopus\ laevis$ egg cells.

When prokaryotic cells are used as the host cells, an expression vector in which an origin that enables replication of the vector in a prokaryotic cell, promoter, ribosome binding site, DNA cloning site, terminator and/or the like is/are contained is used. Examples of the expression vector for $E.\ coli$ include the pUC system, pBluescript II, pET expression system, and pGEX expression system. By incorporating a DNA encoding the above polypeptide into such an expression vector and transforming prokaryotic host cells with the vector, followed by culturing the resulting transformants, the polypeptide encoded by the DNA can be expressed in the prokaryotic host cells. In this process, the polypeptide may also be expressed as a fusion protein with another protein.

When eukaryotic cells are used as the host cells, an expression vector for eukaryotic cells having a promoter, splicing region, poly(A) addition site and/or the like is used as the expression vector. Examples of such an expression vector include pKA1, pCDM8, pSVK3, pMSG, pSVL, pBK-CMV, pBK-RSV, EBV vector, pRS, pcDNA3.1, pSec-Tag(A, B, C), pMSG and pYES2. In the same manner as described above, by incorporating a DNA encoding the above polypeptide into such an expression vector and transforming eukaryotic host cells with the vector, followed by culturing the resulting transformants, the polypeptide encoded by the DNA can be expressed in the eukaryotic host cells. In cases where pIND/V5-His, pFLAG-CMV-2, pEGFP-N1, pEGFP-C1 or the like is used as the expression vector, the above polypeptide may be expressed as a fusion protein wherein a tag, such as a His tag, FLAG tag, myc tag, HA tag or GFP, has been added.

For the introduction of the expression vector into the host cells, well-known methods such as electroporation, the calcium phosphate method, the liposome method, and the DEAE dextran method may be used.

Isolation and purification of the polypeptide of interest from the host cells can be carried out by a combination of known separation operations. Examples of the known separation operations include, but are not limited to, treatment with a denaturant such as urea or with a surfactant; sonication treatment; enzyme digestion; salting-out or solvent fractional precipitation; dialysis; centrifugation; ultrafiltration; gel filtration; SDS-PAGE; isoelectric focusing; ion-exchange chromatography; hydrophobic chromatography; affinity chromatography; and reversed-phase chromatography.

The polypeptides obtained by the above method also include, as mentioned above, those being in the form of a fusion protein with another arbitrary protein. Examples thereof include fusion proteins with glutathione S-transferase (GST) or with a His tag. Such a polypeptide that is in the form of a fusion protein also falls within the scope of the present invention as the above polypeptide (d). Further, in some cases, a polypeptide expressed in a transformed cell is modified in various ways in the cell after translation. Such a post-translationally modified polypeptide also falls within the scope of the present invention as long as it has an immunity-inducing activity. Examples of such a post-translational modification include: elimination of N-terminal methionine; N-terminal acetylation; glycosylation; limited degradation by an intracellular protease; myristoylation; isoprenylation; and phosphorylation.

2. Immunity-Inducing Agent

As described more specifically in Examples described later, a tumor can be regressed by administration of the polypeptide having an immunity-inducing activity to a tumor-bearing living body. Thus, the immunity-inducing agent of the present invention can be used for therapeutic and/or preventive agent of cancers. Further, the polypeptide having an immunity-inducing activity can be used in a method of treating and/or preventing cancers by immunity induction.

Here, the terms "tumor" and "cancer" mean a malignant neoplasm, and are used interchangeably.

In this case, the target cancer, which is not particularly limited, is any cancer that expresses MCEMP1, preferably, a cancer that significantly more highly expresses MCEMP1 than normal cells, specifically, leukemia, myelodysplastic syndrome, osteosarcoma, thymoma, mastocytoma or perianal adenocarcinoma. Examples of these specific cancers include, but are not limited to, acute non-lymphocytic leukemia, chronic lymphocytic leukemia, acute granulocytic leukemia, chronic granulocytic leukemia, acute promyelocytic leukemia, adult T-cell leukemia, aleukemic leukemia, leukocythemic leukemia, basophilic leukemia, blastic leukemia, bovine leukemia, chronic myeloleukemia, leukemia cutis, embryonal leukemia, eosinophilic leukemia, Gross leukemia, Rieder cell leukemia, Schilling's leukemia, stem cell leukemia, subleukemic leukemia, undifferentiated cell leukemia, hairy cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphotropic leukemia, lymphoid leukemia, lymphosarcoma cell leukemia, mast cell leukemia, megakaryocytic leukemia, micromyeloblastic leukemia, monocytic leukemia, myeloblastic leukemia, myeloleukemia, myeloid granulocytic leukemia, myelomonocytic leukemia, Naegeli leukemia, plasma cell leukemia, plasmacytic leukemia, promyelocytic leukemia, refractory anemia (RA), refractory anemia with ringed sideroblasts (RARS), refractory anemia with excess blasts (RAEB), RAEB in transformation (RAEB-T), preleukemia and chronic myelomonocytic leukemia (CMML), conventional central osteosarcoma and subtypes of osteosarcoma (intraosseous well-differentiated osteosarcoma, round cell osteosarcoma, surface osteosarcoma, parosteal osteosarcoma, periosteal osteosarcoma and high-grade surface osteosarcoma), thymoma, mastocytoma, perianal adenoma, and perianal adenocarcinoma.

The subject of interest (i.e., the animal) is preferably a mammal; more preferably a mammal comprising primate, pet animal, any animal raised in zoo or the like, farm animal, and racing animal; and particularly preferably human, dog, or cat.

The administration route of the immunity inducing agent of the present invention to a living body may be either oral administration or parenteral administration, and is preferably, parenteral administration such as intramuscular administration, subcutaneous administration, intravenous administration or intraarterial administration. When the immunity-inducing agent is used for treatment of cancers, it may be administered to a regional lymph node in the vicinity of the tumor to be treated, in order to enhance its anticancer activity. The dose may be any dose as long as the dose is effective for immunity induction, and, for example, in cases where the agent is used in treatment and/or prevention of cancers, the dose may be one effective for treatment and/or prevention of the cancers. The dose effective for treatment and/or prevention of cancers is appropriately selected depending on the size and symptoms of a tumor and the like, and the effective dose is usually 0.0001 µg to 1000 µg, preferably 0.001 µg to 1000 µg per subject animal per day, which may be administered once or in several times. The agent is preferably administered in several times, every several days to several months. As specifically indicated in the Examples below, the immunity-inducing agent of the present invention can cause regression of a tumor. Therefore, since the agent can exert its anticancer activity also against a small number of cancer cells at an early stage, development or recurrence of cancer can be prevented by using the agent before development of the cancer or after treatment of the cancer. Thus, the immunity-inducing agent of the present invention is effective for both treatment and prevention of cancers.

The immunity-inducing agent of the present invention may consist of the polypeptide(s) alone or may be in the form of a preparation obtained by appropriately admixing additives such as pharmacologically acceptable carrier, diluent, excipient, and the like, which are suitable for dosage forms. A method for making a preparation, as well as usable additives, is well known in the field of pharmaceutical preparations, and any methods and additives can be used. Examples of the additives include, are not limited to, diluents such as physiological buffer solutions; excipients such as sugar, lactose, cornstarch, calcium phosphate, sorbitol and glycine; binders such as syrup, gelatin, gum Arabic, sorbitol, polyvinyl chloride and tragacanth; and lubricants such as magnesium stearate, polyethylene glycol, talc and silica. Examples of dosage forms may include oral preparations such as tablets, capsules, granules, powder and syrups; and parenteral preparations such as inhalants, injections, suppositories and solutions. These preparations can be produced by methods generally known in the art.

The immunity-inducing agent of the present invention may be used in combination with an immunoenhancer capable of enhancing the immune response in a living body. The immunoenhancer may be contained in the immunity-inducing agent of the present invention or administered as a separate composition to a patient in combination with the immunity-inducing agent of the present invention.

Examples of the immunoenhancer include adjuvants. Adjuvants can enhance the immune response by providing a reservoir of antigen (extracellularly or within macrophages), activating macrophages and stimulating specific sets of lymphocytes, thereby enhancing the immune response and thus the anticancer action. Therefore, especially in cases where the immunity-inducing agent of the present invention is used for treatment and/or prevention of cancers, the immunity-inducing agent preferably comprises an adjuvant, in addition to the above-described polypeptide that is an effective ingredient. Many types of adjuvants are well-known in the art, and any of these adjuvants may be used. Specific examples of the adjuvants include MPL (SmithKline Beecham), homologues of *Salmonella minnesota* Re 595 lipopolysaccharide obtained after purification and acid hydrolysis of the lipopolysaccharide; QS21 (SmithKline Beecham), pure QA-21 saponin purified from an extract of *Quillja saponaria*; DQS21 described in PCT application WO96/33739 (SmithKline Beecham); QS-7, QS-17, QS-18 and QS-L1 (So and 10 others, "Molecules and Cells", 1997, Vol. 7, p. 178-186); Freund's incomplete adjuvant; Freund's complete adjuvant; vitamin E; Montanide; Alum; CpG oligonucleotides (see, for example, Kreig and 7 others, Nature, Vol. 374, p. 546-549); poly-IC and derivatives thereof (e.g., poly ICLC); and various water-in-oil emulsions prepared from biodegradable oils such as squalene and/or tocopherol. Among them, the preferred are Freund's incomplete adjuvant, Montanide, poly-IC and derivatives thereof, and CpG oligonucleotides. The mixing ratio between the above-described adjuvant and the polypeptide is typically approximately 1:10 to 10:1, preferably approximately 1:5 to 5:1, more preferably approximately 1:1. However, the adjuvant is not limited to the above-described examples, and adjuvants known in the art other than those described above may also be used when the immunity-inducing agent of the present invention is administered (see, for example, Goding, "Monoclonal Antibodies: Principles and Practice, 2nd edition", 1986). Preparation methods for mixtures or emulsions of a polypeptide and an adjuvant are well-known to those skilled in the art of vaccination.

Further, in addition to the above-described adjuvants, factors that stimulate the immune response of interest may be used as the above-described immunoenhancer. For example, various cytokines having a property to stimulate lymphocytes or antigen-presenting cells may be used as the immunoenhancer in combination with the immunity-inducing agent of the present invention. A number of such cytokines capable of enhancing the immune response are known to those skilled in the art, and examples thereof include, but are not limited to, interleukin-12 (IL-12), GM-CSF, IL-18, interferon-α, interferon-β, interferon-ω, interferon-γ, and Flt3 ligand, which have been reported to enhance the prophylactic action of vaccines. Such factors may be used as the immunoenhancer and administered to a patient by adding it to the immunity-inducing agent of the present invention or administered as an independent composition in combination with the immunity-inducing agent of the present invention.

3. Antigen-Presenting Cells or Cytotoxic T Cells

The present invention further provides a method for preparing an antigen-presenting cell containing a complex of the polypeptide as mentioned above and an MHC molecule, comprising contacting the polypeptide with an antigen-presenting cell from a subject ex vivo or in vitro.

The present invention also provides an antigen-presenting cell characterized by containing a complex of the polypeptide as mentioned above and an MHC molecule and obtained by the method.

By bringing the above-described polypeptide into contact with antigen-presenting cells ex vivo or in vitro, the antigen-presenting cells can be made to present the polypeptide. That is, the polypeptides (a) to (d) described above can be used as the agent for treating antigen-presenting cells. Herein, examples of the antigen-presenting cells which may be preferably used include dendritic cells or B cells having an MHC class I molecule. Various MHC class I molecules have been identified and are well-known. MHC molecules in human are called HLA. Examples of HLA class I molecules include HLA-A, HLA-B and HLA-C, more specifically, HLA-A1, HLA-A0201, HLA-A0204, HLA-A0205, HLA-A0206, HLA-A0207, HLA-A11, HLA-A24, HLA-A31, HLA-A6801, HLA-B37, HLA-B8, HLA-B2705, HLA-B37, HLA-Cw0401 and HLA-Cw0602.

The dendritic cells or B cells having an MHC class I molecule can be prepared from peripheral blood by a well-known method. For example, tumor-specific dendritic cells can be induced by inducing dendritic cells from bone marrow, umbilical cord blood or patient's peripheral blood using granulocyte-macrophage colony-stimulating factor (GM-CSF) and IL-3 (or IL-4), and then adding a tumor-associated peptide to the culture system.

By administering an effective amount of such dendritic cells, a response desired for therapy of a cancer can be induced. As the cells to be used, bone marrow or umbilical cord blood donated by a healthy individual, or bone marrow, peripheral blood or the like from the patient himself may be used. When autologous cells of the patient are used, high safety can be attained and serious side effects are expected to be avoided. The peripheral blood or bone marrow may be any of fresh sample, cold-stored sample and frozen sample. As for the peripheral blood, whole blood may be cultured or the leukocyte components alone may be separated and cultured, and the latter is more efficient and thus preferred. Further, among the leukocyte components, mononuclear cells may be separated. In cases where the cells are originated from bone marrow or umbilical cord blood, the whole cells constituting the bone marrow may be cultured, or mononuclear cells may be separated therefrom and cultured. Peripheral blood, the leukocyte components thereof and bone marrow cells contain mononuclear cells, hematopoietic stem cells and immature dendritic cells, from which dendritic cells are originated, and also CD4-positive cells and the like. As for the cytokine to be used, the production method thereof is not restricted, and a naturally-occurring or recombinant cytokine or the like may be employed as long as its safety and physiological activity have been confirmed. Preferably, a preparation with assured quality for medical use is used in a minimum necessary amount. The concentration of the cytokine(s) to be added is not restricted as long as the dendritic cells are induced at the concentration, and usually, the total concentration of the cytokine(s) is preferably approximately 10-1000 ng/mL, more preferably approximately 20-500 ng/mL. The cultivation may be carried out using a well-known medium usually used for cultivation of leukocytes. The culturing temperature is not restricted as long as proliferation of the leukocytes is attained at the temperature, and a temperature of about 37° C., which is the body temperature of human, is most preferred. The atmospheric environment during the culturing is not restricted as long as proliferation of the leukocytes is attained under the environment, and 5% $CO_2$ is preferably ventilated. The culturing period is not restricted as long as a necessary number of the cells are induced during such period, being usually 3 days to 2 weeks. As for the apparatuses used for separation and cultivation of the cells, appropriate apparatuses, preferably those whose safety upon application to medical uses have been confirmed and whose operations are stable and simple, may be employed. In particular, as for the cell-culturing apparatus, not only a general vessel such as Petri dish, flask or bottle, but also a layer type vessel, multistage vessel, roller bottle, spinner type bottle, bag type culturing vessel, hollow fiber column or the like may be used.

The method itself of contacting the polypeptide as mentioned above with an antigen-presenting cell ex vivo or in vitro, can be carried out by a method well known in the art, for example, by culturing the antigen-presenting cell in a culture liquid containing the polypeptide. The concentration of the peptide in the medium, which is not particularly limited, is usually approximately 1 to 100 µg/ml and preferably approximately 5 to 20 µg/ml. The cell density during culturing, which is not particularly limited, is usually approximately $10^3$ to $10^7$ cells/ml and preferably approximately $5\times10^4$ to $5\times10^6$ cells/ml. The culture is preferably carried out by routine methods at 37° C. in 5% $CO_2$ atmosphere. The length of a peptide that can be presented by the antigen-presenting cell on the surface thereof is usually approximately 30 amino acid residues at a maximum. Accordingly, when the antigen-presenting cell is contacted with the polypeptide ex vivo or in vitro, the polypeptide may be prepared so as to have a length of approximately 30 amino acid residues or less; however, the length is not limited to this.

By culturing the antigen-presenting cell in the presence of the above polypeptide, the peptide is integrated into an MHC molecule of the antigen-presenting cell and presented on the surface of the antigen-presenting cell. Accordingly, it is possible to prepare an isolated antigen-presenting cell containing a complex of the polypeptide and the MHC molecule. Such an antigen-presenting cell can present the polypeptide in vivo, ex vivo or in vitro to a T cell and can induce and proliferate a cytotoxic T cell specific to the polypeptide.

The present invention further provides a method for preparing a cytotoxic T cell specific to the polypeptide as mentioned above, comprising contacting the antigen-presenting cells with a T cell from a subject ex vivo or in vitro to activate the T cell.

The present invention also provides a cytotoxic T cell specific to the polypeptide as mentioned above, obtained by this method.

By contacting an antigen-presenting cell, which contains a complex of the polypeptide as mentioned above and an MHC molecule, prepared in the above-mentioned manner with a T cell ex vivo or in vitro, the cytotoxic T cell specific to the polypeptide can be induced and proliferated. The contact can be made by co-culturing the antigen-presenting cell and the T cell in a liquid medium; for example, by suspending the antigen-presenting cell in a liquid medium, placing the resultant suspension in a container such as wells of a micro plate, adding the T cell to the wells, and culturing them. The mixing ratio of the antigen-presenting cell and the T cell during the co-culture, which is not particularly limited, is usually, approximately 1:1 to 1:100, preferably approximately 1:5 to 1:20 in terms of a ratio of the numbers of the cells. The density of the antigen-presenting cell in the liquid medium, which is not particularly limited, is usually, approximately 100 to 10,000,000 cells/ml and preferably approximately 10,000 to 1,000,000 cells/ml. The co-culture is preferably carried out by routine methods at 37° C. in 5% $CO_2$ atmosphere. The culture time, which is not particularly limited, is usually, 2 days to 3 weeks and preferably about 4 days to 2 weeks. The co-culture is preferably carried out in the presence of one or more types of interleukins such as IL-2, IL-6, IL-7 and IL-12. In this case, the concentrations of IL-2 and IL-7 are usually approximately 5 to 20 U/ml, the concentration of IL-6 is usually approximately 500 to 2000 U/ml, and the concentration of IL-12 is usually approximately 5 to 20 ng/ml; however, the concentrations are not limited to these. The co-culture may be repeated once or several times by supplementing the fresh antigen-presenting cells. For example, an operation, which comprises discarding the culture supernatant after co-culture, adding a suspension of the fresh antigen-presenting cells, and carrying out co-culture, may be repeated once or several times. The co-culturing conditions may be the same as above.

Through the co-culture, the cytotoxic T cell specific to the polypeptide is induced and proliferated. Accordingly, the above-mentioned polypeptide can use to prepare isolated T cells that selectively bind a complex of the polypeptide and the MHC molecule.

As described in Examples below, the MCEMP1 gene is specifically expressed in leukemia, myelodysplastic syndrome, osteosarcoma, thymoma, mastocytoma or perianal adenocarcinoma. Accordingly, in these cancers, it is thought that MCEMP1 is significantly more largely present than in normal cells. Accordingly, if the cytotoxic T cell prepared in the above-described manner is administered in vivo and a part of the MCEMP1 polypeptide existing in cancer cells is presented by the MHC molecule on the surface of a cancer cell, the cytotoxic T cell can damage the cancer cell by using the part of the MCEMP1 polypeptide as a marker. The antigen-presenting cell presenting a part of the MCEMP1 polypeptide can induce and proliferate the cytotoxic T cell specific to the polypeptide in vivo. Thus, cancer cells can also be damaged by administering the antigen-presenting cell to a living body. More specifically, the cytotoxic T cell and the antigen-presenting cell prepared by use of the above-mentioned polypeptide are also useful for treating and/or preventing cancer similarly to the immunity-inducing agent of the present invention.

In cases where the above-described isolated antigen-presenting cells or isolated T cells are administered to a living body, these are preferably prepared by treating antigen presenting cells or T cells collected from the patient to be treated with the polypeptide (a) to (d) as described above in order to avoid the immune response in the living body that attacks these cells as foreign bodies.

The treating and/or preventing agent for cancer comprising, as an effective ingredient, antigen-presenting cells or T cells is preferably administered via a parenteral administration route, for example, by intravenous or intraarterial administration. The dose is appropriately selected depending on the symptoms, the purpose of administration and the like, and is usually 1 cell to 10,000,000,000,000 cells, preferably 1,000,000 cells to 1,000,000,000 cells, which dose is preferably administered once every several days to once every several months. The preparation may be, for example, the cells suspended in physiological buffered saline, and the preparation may be used in combination with other anticancer agent(s), cytokine(s) or the like. Further, one or more additives well-known in the field of pharmaceuticals may also be added.

4. DNA Vaccine

By expressing a polynucleotide encoding any of the polypeptides (a) to (d) in the body of a subject animal, antibody production and cytotoxic T cells can also be induced in the living body, and an effect comparable to that obtained in the case of administration of the polypeptide can be obtained. That is, the immunity-inducing agent of the present invention may be the one comprising, as an active ingredient, a recombinant vector having a polynucleotide encoding any of the polypeptides (a) to (d), wherein the recombinant vector is capable of expressing the polypeptide in a living body. Such a recombinant vector capable of expressing an antigenic polypeptide as shown in Examples described below is also called a DNA vaccine.

The vector used for production of the DNA vaccine is not restricted as long as it is a vector capable of expressing the polypeptide in a cell of a subject animal (preferably in a mammalian cell), and may be either a plasmid vector or a virus vector, and any vector known in the field of DNA vaccines may be used. The polynucleotide such as DNA or RNA encoding the above-described polypeptide can be easily prepared as mentioned above by a conventional method. Incorporation of the polynucleotide into the vector can be carried out using a method well-known to those skilled in the art.

The administration route of the DNA vaccine is preferably a parenteral route such as intramuscular, subcutaneous, intravenous or intraarterial administration, and the dose may be appropriately selected depending on the type of the antigen and the like, and is usually approximately 0.1 µg to 100 mg, preferably approximately 1 µg to 10 mg in terms of the weight of the DNA vaccine per 1 kg of body weight.

Examples of the method using a virus vector include methods in which a polynucleotide encoding the above-described polypeptide is incorporated into an RNA virus or DNA virus, such as a retrovirus, adenovirus, adeno-associated virus, herpes virus, vaccinia virus, pox virus, poliovirus or Sindbis virus, and then a subject animal is infected with the resulting virus. Among these methods, those using a retrovirus, adenovirus, adeno-associated virus, vaccinia virus or the like are especially preferred.

Examples of other methods include a method wherein an expression plasmid is directly intramuscularly administered (DNA vaccine method), a liposome method, a lipofectin method, a microinjection method, a calcium phosphate method and an electroporation method, and the DNA vaccine method and the liposome method are especially preferred.

Methods for actually allowing a gene encoding the above-described polypeptide used in the present invention to act as a drug include an in vivo method wherein the gene is directly introduced into the body, and an ex vivo method wherein a certain kind of cells are collected from a subject animal and the gene is introduced into the cells outside the body, followed by returning the cells to the body (Nikkei Science, 1994, April, p. 20-45; The Pharmaceutical Monthly, 1994, Vol. 36, No. 1, p. 23-48; Experimental Medicine, Extra Edition, 1994, Vol. 12, No. 15; and references cited in these literatures, and the like). The in vivo method is more preferred.

When the gene is administered by the in vivo method, it may be administered through an appropriate administration route depending on a disease to be treated, symptom and so on. The gene may be administered by, for example, intravenous, intraarterial, subcutaneous or intramuscular administration. When the gene is administered by the in vivo method, it may be formulated into a preparation such as a solution, and in general, it is formulated into an injection solution or the like containing DNA encoding the above-described polypeptide of the present invention as an active ingredient, and where needed, a routine carrier may be further added to the solution. In the case of a liposome or membrane fusion liposome (e.g., Sendai virus (HVJ)-liposome) containing the DNA, the liposome may be formulated into a liposome preparation such as a suspension, a frozen preparation, or a centrifugally concentrated frozen preparation.

Herein, for example, "the nucleotide sequence represented by SEQ ID NO: 1" includes not only the nucleotide sequence represented by SEQ ID NO: 1 itself, but also the sequence complementary thereto. Thus, for example, "the polynucleotide having the nucleotide sequence represented by SEQ ID NO: 1" includes a single-stranded polynucleotide having the nucleotide sequence represented by SEQ ID NO: 1 itself, a single-stranded polynucleotide having the nucleotide sequence complementary thereto, and a double-stranded polynucleotide composed of these single-stranded polynucleotides. When a polynucleotide encoding a polypeptide used in the present invention is prepared, any one of these nucleotide sequences is appropriately selected, and those skilled in the art can easily carry out the selection.

EXAMPLES

Now, the present invention will be more specifically described below based on Examples. However, the scope of the present invention is not limited by Examples.

Example 1

Obtaining Novel Cancer Antigen Protein by SEREX Method (1) Preparation of cDNA Library Total RNA was extracted from canine testes in accordance with the Acid-guanidium-Phenol-Chloroform method, and then, poly(A) RNA was purified by using Oligotex-dT30 mRNA purification Kit (Takara Shuzo Co., Ltd.) in accordance with the protocol attached to the kit.

Using the obtained mRNA (5 µg), a cDNA phage library was synthesized. For the preparation of the cDNA phage library, cDNA Synthesis kit, Zap-cDNA Synthesis Kit, or ZAP-cDNA GigapackIII Gold Cloning Kit (STRATAGENE) was used in accordance with the protocol attached to the kit. The size of the prepared cDNA phage library was $1 \times 10^6$ pfU/ml.

(2) Screening of cDNA Library with Serum

Using the prepared cDNA phage library, immunoscreening was carried out. More specifically, host *E. coli* (XL1-Blue MRF') was infected with the phage so as to obtain approximately 2500 clones in an NZY agarose plate of φ90×15 mm and cultured at 42° C. for 3-4 hours to obtain plaques. The plate was covered with nitrocellulose membrane (Hybond C Extra: GE Healthcare Bio-Science) impregnated with IPTG (isopropyl-β-D-thiogalactoside) at 37° C. for 4 hours to induce protein expression and the protein was transferred to the membrane. Thereafter, the membrane was taken, soaked in TBS (10 mM Tris-HCl, 150 mM NaCl pH7.5) containing 0.5% of skim milk powder, and shaken at 4° C. overnight to suppress a nonspecific reaction. This filter was allowed to react with the 500-fold diluted serum of a canine patient at room temperature for 2 to 3 hours.

As the sera of canine patients mentioned above, the sera taken from leukemia dogs were used. The sera were stored at −80° C. and pretreated immediately before use. The method of the pretreatment of the sera was as follows. That is, first, the host *Escherichia coli* (XL1-Blue MRF) was infected with λ ZAP Express phage into which no foreign gene was inserted, and then cultured on a NZY plate medium at 37° C. overnight. Subsequently, 0.2 M NaHCO₃ buffer (pH8.3) containing 0.5 M NaCl was added to the plate, and the plate was left to stand at 4° C. for 15 hours, followed by collecting the supernatant as an *Escherichia coli*/phage extract. Thereafter, the collected *Escherichia coli*/phage extract was allowed to flow through a NHS-column (GE Healthcare Bio-Science) to immobilize proteins derived from *Escherichia coli*/phage onto the column. The serum from the canine patient was allowed to flow through and to react with the protein-immobilized column to remove antibodies adsorbed to *Escherichia coli* and phage from the serum. The serum fraction passed though the column was diluted 500 fold with TBS containing 0.5% of skim milk powder, and the resulting diluent was used as a material for immunoscreening.

The above membrane on which the thus treated serum and the proteins were blotted was washed 4 times with TBS-T (0.05% Tween 20/TBS), and allowed to react with goat anti-dog IgG (Goat anti Dog IgG-h+L HRP conjugated; BETHYL Laboratories) 5,000-fold diluted with TBS containing 0.5% skim milk powder as a secondary antibody at room temperature for 1 hour, followed by detection by the enzyme coloring reaction using the NBT/BCIP reaction solution (Roche). Colonies at positions where a positive coloring reaction was observed were recovered from the NZY agarose plate having a size of Φ90×15 mm, and dissolved in 500 µl of SM buffer (100 mM NaCl, 10 mM MgClSO$_4$, 50 mM Tris-HCl, 0.01% gelatin; pH 7.5). The screening was repeated as a second and third screening in the same manner as described above until a single coloring reaction-positive colony was obtained, thereby isolating one positive clone after screening of approximately 10,000 phage clones reactive with IgG in the serum.

(3) Sequence-Identity Search of Isolated Antigen Gene

In order to subject the single positive clone isolated by the above-described method to nucleotide sequence analysis, an operation for conversion of the phage vector to a plasmid vector was carried out. Specifically, a solution (200 µL) containing host *Escherichia coli* (XL1-Blue MRF) prepared so as to show an absorbance OD$_{600}$ of 1.0, a purified phage solution (100 µL), and further 1 µL of ExAssist helper phage (STRATAGENE) were mixed and allowed to react at 37° C. for 15 minutes. LB medium (3 mL) was added and cultivation was carried out at 37° C. for 2.5-3 hours. The resulting culture was immediately kept in a water bath at 70° C. for 20 minutes, and then was centrifuged at 4° C. at 1000×g for 15 minutes to collect the supernatant as a phargemid solution. Subsequently, a solution (200 µL) containing a phargemid host *Escherichia coli* (SOLR) prepared so as to have an absorbance OD$_{600}$ of 1.0 and the purified phage solution (10 µL) were mixed and allowed to react at 37° C. for 15 minutes. The resultant solution (50 µL) was seeded on an ampicillin (final concentration: 50 µg/mL)-containing LB agar medium and cultured at 37° C. overnight. A single transformed SOLR colony was picked up, cultured in ampicillin (final concentration: 50 µg/mL)-containing LB medium at 37° C. and, thereafter, purified by QIAGEN plasmid Miniprep Kit (QIAGEN) to obtain a plasmid DNA having a desired insert.

The purified plasmid was subjected to the primer walking using T3 primer represented by SEQ ID NO: 9 and T7 primer represented by SEQ ID NO: 10 to analyze the full-length sequence of the insert. The gene sequence represented by SEQ ID NO: 3 was obtained by the sequencing analysis. Using the nucleotide sequence of the gene and amino acid sequence therefor, the sequence identity search, which is a search for sequence identity with known genes, was carried out by the sequence identity search program BLAST search (http://www.ncbi.nlm.nih.gov/BLAST/). As a result, it was found that the gene obtained above is MCEMP1 gene. In the human MCEMP1, which is a human homolog of canine MCEMP1, the nucleotide-sequence identity was 70% and the amino acid sequence identity was 51%. In cat homolog, i.e., cat MCEMP1, the nucleotide sequence identity was 83% and the amino acid sequence identity was 64%. In mouse homolog, i.e., mouse MCEMP1, the nucleotide sequence identity was 65% and the amino acid sequence identity was 47%. The nucleotide sequence of the human MCEMP1 is represented by SEQ ID NO: 1 and the amino acid sequences thereof are represented by SEQ ID NO: 2. The nucleotide sequence of the cat MCEMP1 is represented by SEQ ID NO: 5 and the amino acid sequence therefor is represented by SEQ ID NO: 6. The nucleotide sequence of the mouse MCEMP1 is represented by SEQ ID NO: 7 and the amino acid sequence thereof is represented by SEQ ID NO: 8.

(4) Gene Expression Analysis in Different Tissues

Figure 2:
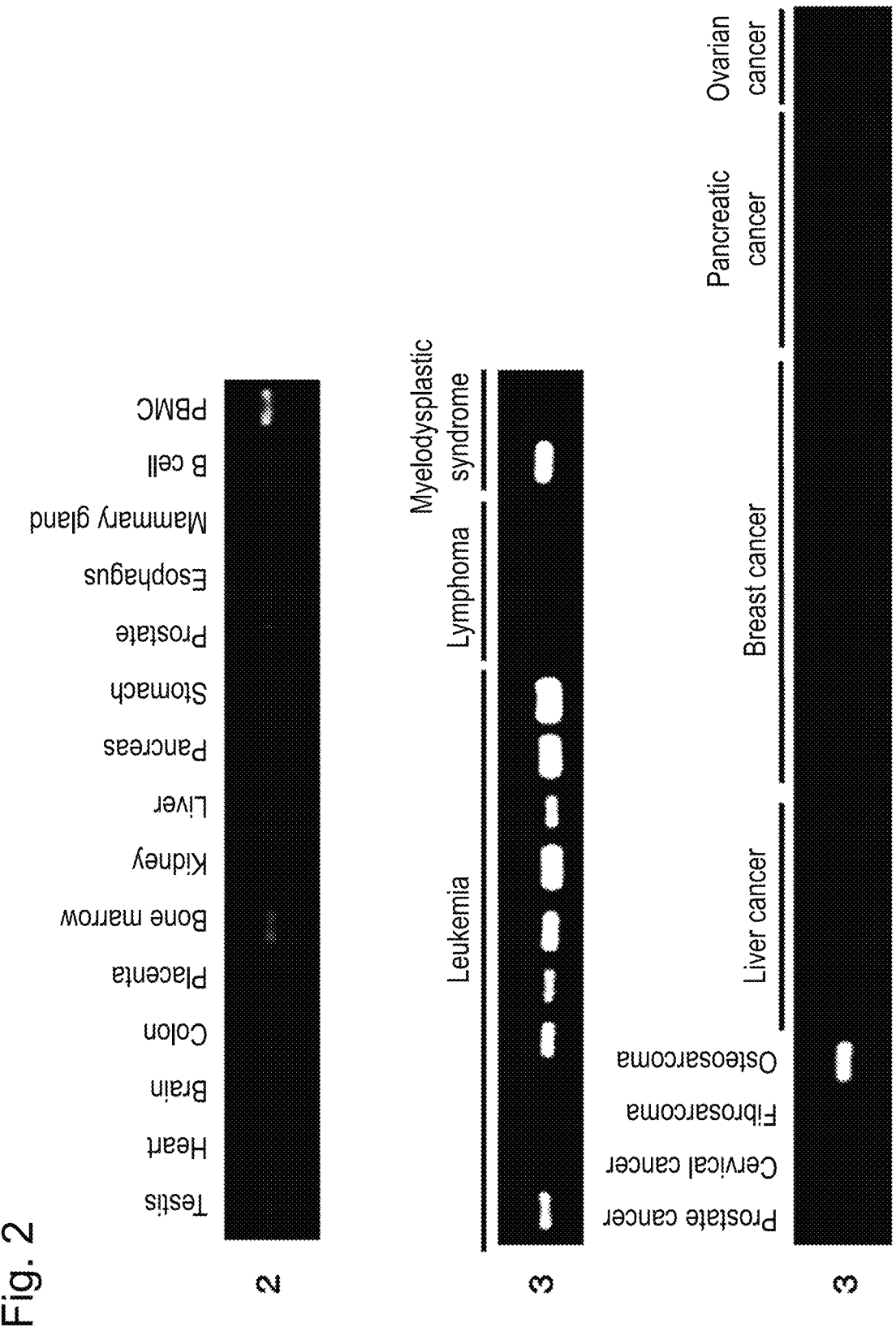
FIG. 2 This figure shows expression patterns of MCEMP1 gene in individual human tissues and cancer cell lines. Reference number 2 shows expression patterns of the human MCEMP1 gene in individual human normal tissues; and reference number 3 shows expression patterns of the human MCEMP1 gene in individual human cancer cell lines. In the figure, PBMC represents peripheral blood mononuclear cells.
Figure 3:
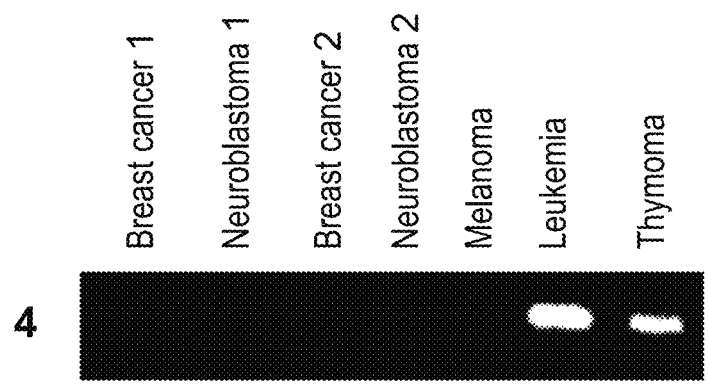
FIG. 3 This figure shows expression patterns of the identified MCEMP1 gene in individual mouse cancer cell lines. Reference number 4 shows expression patterns of the mouse MCEMP1 gene in individual mouse cancer cell lines.

Expression of the genes obtained by the above method in normal tissues and tumor tissues and cancer cell lines from dogs, humans and mice was examined by a RT-PCR (Reverse Transcription-PCR) method. The reverse transcription reaction was carried out as follows. First, total RNAs were extracted from individual tissues (50-100 mg) and individual cell lines (5-10×10$^6$ cells) by use of TRIZOL reagent (Life technology) in accordance with the protocol attached. Using the total RNAs, cDNAs were synthesized by using Superscript First-Strand Synthesis System for RT-PCR (Life technology) in accordance with the protocol attached. As the cDNAs of the human normal tissues (from the brain, testis, colon, and placenta), gene pool cDNA (Life technology), QUICK-Clone cDNA (Clontech) and Large-Insert cDNA Library (Clontech) were used. The PCR reaction was carried out by using the gene specific primers obtained (canine primers are represented by SEQ ID NOs: 11 and 12, human primers are represented by SEQ ID NO: 13 and 14, mouse primers are represented by SEQ ID NOs: 15 and 16), as follows. That is, reagents were added to the attached buffer wherein the reagents contain 0.25 µL of the sample prepared by the reverse transcription reaction, the above primers (2 µM for each), dNTPs (0.2 mM for each) and a 0.65 U ExTaq polymerase (Takara Shuzo Co., Ltd.). The reaction mixture 25 µL in total was subjected to PCR using a Thermal Cycler (BIO RAD). In the PCR, 30 cycles were repeated wherein one cycle consists of the treatments: at 94° C. for 30 seconds; 55° C. for 30 seconds; and at 72° C. for one minute. As a result, as shown in FIG. 1, the canine MCEMP1 gene was strongly expressed in canine tumor tissues, i.e., mastocytoma and perianal adenocarcinoma tissues (FIG. 1). The human MCEMP1 gene was not expressed in almost all normal human tissues, but it was strongly expressed in human cancer cells, i.e., leukemia, myelodysplastic syndrome, and osteosarcoma cell lines (FIG. 2). Furthermore, the expression of the mouse MCEMP1 gene was detected in leukemia and thymoma cell lines (FIG. 3).

Example 2

Analysis for Cancer Antigenicity of MCEMP1 In Vivo (1) Preparation of Recombinant Vector Expressing Mouse MCEMP1 In Vivo A recombinant vector expressing mouse MCEMP1 in vivo was prepared based on the nucleotide sequence represented by SEQ ID NO: 7 in accordance with the following method. PCR was carried out as follows. A reaction mixture was prepared by adding reagents: cDNAs (1 µL), which were prepared from mouse leukemia cell line EL4 (purchased from ATCC) whose expression was observed in Example 1, two types of primers (0.4 µM for each) having EcoRI and NotI restriction enzyme cleaved sequences (represented by SEQ ID NOs: 17 and 18), 0.2 mM dNTPs, and 1.25 U PrimeSTAR HS polymerase (Takara Shuzo Co., Ltd.), and the attached buffer so as to obtain a total amount of 50 µL; and subjected to PCR using a Thermal Cycler (BIO RAD). In the PCR, 30 cycles were repeated wherein one cycle consists of the treatments: at 98° C. for 10 seconds; at 55° C. for 15 seconds; and at 72° C. for 1 minute. The above-mentioned two types of primers were used for amplifying a region encoding a full-length amino acid sequence represented by SEQ ID NO: 8. After the PCR, the amplified DNA was electrophoresed on 1% agarose gel, and a DNA fragment of approximately 550 bp was purified by use of QIAquick Gel Extraction Kit (QIAGEN).

The purified DNA fragment was ligated to the cloning vector pCR-Blunt (Life technology), which vector was then transformed into E. coli cells, followed by collecting the plasmid vector. By its sequencing, it was confirmed that the sequence of the amplified gene fragment was identical with a desired sequence. The plasmid whose sequence was identical with the desired sequence was treated with EcoRI and NotI restriction enzymes. After purification was carried out with QIAquick Gel Extraction Kit, the desired gene sequence was inserted into the mammalian expression vector pcDNA3.1 (Invitrogen) treated with EcoRI and NotI restriction enzymes (hereinafter referred to as mouse MCEMP1/pcDNA3.1). Owing to the use of the vector, mouse MCEMP1 protein is produced in a mammalian cell.

To the plasmid DNA (100 μg) prepared above, 50 μg of gold particles (Bio Rad), spermidine (100 μl) (SIGMA) and 1M CaCl$_2$ (100 μl (SIGMA)) were added. The mixture was stirred by a vortex and allowed to stand for 10 minutes at room temperature (hereinafter referred to as "gold-DNA particles"). After centrifugation at 3000 rpm for one minute, the supernatant was discarded, followed by washing the pellet three times with 100% ethanol (WAKO). To the gold-DNA particles, 100% ethanol (6 ml) was added, and the mixture was stirred sufficiently by a vortex. The gold-DNA particles were poured in Tefzel Tubing (Bio Rad) to precipitate them on its wall. The Tefzel Tubing with attached gold-DNA particles was dried in the air by removing ethanol and thereafter cut into pieces having a length suitable for use in gene gun (hereinafter referred to as mouse MCEMP1/tube).

(2) Antitumor Effect of Mouse MCEMP1 by DNA Vaccine Method-1

Five A/J mice (7 weeks old, male, purchased from Japan SLC, Inc.) were used. The tube (mouse MCEMP1/tube) prepared above was immobilized on a gene gun. A DNA vaccine was percutaneously administered to the shaved peritoneal cavity of mice with the help of pure helium gas at a pressure of 400 psi three times in total every 7 days (plasmid DNA inoculation amount: 2 μg/animal). After the percutaneous administration, the mouse leukemia cell line EL4 cells, which were found to express the MCEMP1 gene in Example 1, were grafted to each mouse to evaluate the antitumor effect (referred to as a prevention model). For the control, the plasmid DNA without inserted mouse MCEMP1 gene was administered to 5 mice in the prevention model.

The antitumor effect was evaluated for the size of a tumor (long diameter×(short diameter)$^2$/2) and the rate of surviving mice. As the result, in the prevention model, the tumor sizes after 28 days of the control group and the mouse MCEMP1 plasmid administration group were 1153 mm$^3$ and 480 mm$^3$, respectively. Thus, it was found that the tumor size was significantly reduced in the mouse MCEMP1 plasmid administration group. As the result that the survival situation was observed in the prevention model, the whole cases of the control group died 59 days after administration; whereas in the mouse MCEMP1 plasmid administration group, 60% of the mice were alive. From these results, the significant antitumor effect on the mouse MCEMP1 plasmid administration group compared to the control group was demonstrated.

(3) Antitumor Effect of Mouse MCEMP1 by DNA Vaccine Method-2

Five A/J mice (7 weeks old, male, purchased from Japan SLC, Inc.) were used. The tube (mouse MCEMP1/tube) prepared above was immobilized on a gene gun. A DNA vaccine was percutaneously administered to the shaved peritoneal cavity of mice with the help of pure helium gas at a pressure of 400 psi three times in total every 7 days (plasmid DNA inoculation amount: 2 μg/animal). After the percutaneous administration, the mouse leukemia cell line EG7 cells, which were found to express the MCEMP1 gene in Example 1, were grafted to each mouse to evaluate the antitumor effect (referred to as a prevention model). For the control, the plasmid DNA without inserted mouse MCEMP1 gene was administered to 5 mice in the prevention model group.

The antitumor effect was evaluated for the size of a tumor (long diameter×(short diameter)$^2$/2) and the rate of surviving mice. As the result, in the prevention model, the tumor sizes after 28 days of the control group and the mouse MCEMP1 plasmid administration group were 982 mm$^3$ and 521 mm$^3$, respectively. Thus, it was found that the tumor size was significantly reduced in the mouse MCEMP1 plasmid administration group. As the result that the survival situation was observed in the prevention model, the whole cases of the control group died 68 days after administration; whereas in the mouse MCEMP1 plasmid administration group, 60% of the mice were alive. From these results, the significant antitumor effect on the mouse MCEMP1 plasmid administration group compared to the control group was demonstrated.

(4) Preparation of Recombinant Vector Expressing Human MCEMP1 In Vivo

A recombinant vector expressing human MCEMP1 in vivo was prepared based on the nucleotide sequence represented by SEQ ID NO: 1 in accordance with the following method. PCR was carried out as follows. A reaction mixture was prepared by adding reagents: cDNAs (1 μL), which were prepared from the human leukemia cell line U937 (purchased from ATCC) whose expression was observed in Example 1, two types of primers (0.4 μM for each) having EcoRI and NotI restriction enzyme cleaved sequences (represented by SEQ ID NOs: 19 and 20), 0.2 mM dNTPs, and 1.25 U PrimeSTAR HS polymerase (Takara Shuzo Co., Ltd.), and the attached buffer so as to obtain a total amount of 50 μL; and subjected to PCR using a Thermal Cycler (BIO RAD). In the PCR, 30 cycles were repeated wherein one cycle consists of the treatments: at 98° C. for 10 seconds; at 55° C. for 15 seconds; and at 72° C. for 1 minute. The above-mentioned two types of primers were used for amplifying a region encoding the full-length amino acid sequence represented by SEQ ID NO: 2. After the PCR, the amplified DNA was electrophoresed on 1% agarose gel, and a DNA fragment of approximately 550 bp was purified by use of QIAquick Gel Extraction Kit (QIAGEN).

The purified DNA fragment was ligated to the cloning vector pCR-Blunt (Life Technology), which vector was then transformed into E. coli cells, followed by collecting the plasmid vector. By its sequencing, it was confirmed that the sequence of the amplified gene fragment was identical with a desired sequence. The plasmid whose sequence was identical with the desired sequence was treated with EcoRI and NotI restriction enzymes. After purification was carried out with QIAquick Gel Extraction Kit, the desired gene sequence was inserted into the mammalian expression vector pcDNA3.1 (Invitrogen) treated with EcoRI and NotI restriction enzymes (hereinafter referred to as human MCEMP1/pcDNA3.1). Owing to the use of the vector, human MCEMP1 protein is produced in a mammalian cell.

To plasmid DNA (100 μg) prepared above, 50 μg of gold particles (Bio Rad), spermidine (100 μl) (SIGMA) and 1 M CaCl$_2$ (100 μl (SIGMA)) were added. The mixture was stirred by a vortex and allowed to stand for 10 minutes at room temperature (hereinafter referred to as gold-DNA particles). After centrifugation at 3000 rpm for one minute, the supernatant was discarded, followed by washing the pellet three times with 100% ethanol (WAKO). To the gold-DNA particles, 100% ethanol (6 ml) was added, and the mixture was stirred sufficiently by a vortex. The gold-DNA particles were poured in Tefzel Tubing (Bio Rad) to precipitate them on its wall. The Tefzel Tubing with attached gold-DNA particles was dried in the air by removing ethanol and thereafter cut into pieces having a length suitable for use in gene gun (hereinafter referred to as human MCEMP1/tube).

(5) Establishment of Cells Stably Expressing Full-Length Human MCEMP1

Human MCEMP1/pcDNA3.1 prepared above was introduced by the lipofection method into mouse neuroblastoma cell line N2a cells (ATCC), and then, selection was performed using 500 μg/ml G418 (Nacalai Tesque, Inc.) to establish a N2a cell line stably expressing full-length human MCEMP1 (N2a-human MCEMP1). Cells obtained by introducing an expression vector (hereinafter referred to as emp/pcDNA3.1) without inserted cDNA encoding human MCEMP1 and then performing selection in the same manner as described above were used as control cells (hereinafter referred to as N2a-emp).

(6) Antitumor Effect of Human MCEMP1 by DNA Vaccine Method

Five A/J mice (7 weeks old, male, purchased from Japan SLC, Inc.) were used. The tube (human MCEMP1/tube) prepared above was immobilized on a gene gun. A DNA vaccine was percutaneously administered to the shaved peritoneal cavity of mice with the help of pure helium gas at a pressure of 400 psi three times in total every 7 days (plasmid DNA inoculation amount: 2 μg/animal). After the percutaneous administration, N2a-human MCEMP1 or N2a-emp as control cells prepared above was grafted to each mouse to evaluate the antitumor effect (referred to as a prevention model). For the control, the plasmid DNA without inserted human MCEMP1 gene was administered to 5 mice in the prevention model.

The antitumor effect was evaluated for the size of a tumor (long diameter×(short diameter)$^2$/2) and the rate of surviving mice. As the result, in the prevention model of N2a-human MCEMP1, the tumor sizes after 28 days of the control group and the human MCEMP1 plasmid administration group were 1379 mm$^3$ and 513 mm$^3$, respectively. Thus, it was found that the tumor size was significantly reduced in the human MCEMP1 plasmid administration group. As the result that the survival situation was observed in the prevention model, the whole cases of the control group died 61 days after administration; whereas in the human MCEMP1 plasmid administration group, 60% of the mice were alive. From these results, the significant antitumor effect on the human MCEMP1 plasmid administration group compared to the control group was demonstrated in the prevention model of N2a-human MCEMP1. On the other hand, no significant antitumor effect on the human MCEMP1 plasmid administration group compared to the control group was demonstrated in the prevention model of N2a-emp.

INDUSTRIAL APPLICABILITY

The present invention provides an immunity-inducing agent comprising a polypeptide exhibiting an antitumor activity to cancers and thus is useful for treating and/or preventing cancers.

All publications, patents and patent applications cited herein are incorporated by reference in their entirety.

The invention claimed is:

1. A method for inducing immunity to treat and/or prevent MCEMP1 expressing cancer in a subject in need thereof, comprising administering, to the subject, an immunity-inducing agent, as a therapeutic and/or preventive agent for MCEMP1 expressing cancer, comprising an MCEMP1 polypeptide having immunity-inducing activity and selected from the group consisting of the following polypeptides (a), or a recombinant vector comprising a polynucleotide encoding the polypeptide and capable of expressing said polypeptide in vivo:

(a) MCEMP1 polypeptides consisting of the amino acid sequences represented by SEQ ID NO: 2, 4, 6, and 8 in the Sequence Listing.

2. The method according to claim 1, wherein the immunity-inducing agent is an agent for treating antigen-presenting cells.

3. The method according to claim 1, wherein the cancer is leukemia, myelodysplastic syndrome, osteosarcoma, thymoma, mastocytoma or perianal adenocarcinoma.

4. The method according to claim 1, wherein the immunity-inducing agent further comprises an immunoenhancer.

5. The method according to claim 4, wherein the immunoenhancer is at least one selected from the group consisting of Freund's incomplete adjuvant, Montanide, Poly IC and derivatives thereof, CpG oligonucleotides, interleukin 12, interleukin 18, interferon α, interferon β, interferon ω, interferon γ, and Flt 3 ligand.

6. The method according to claim 2, wherein the immunity-inducing agent further comprises an immunoenhancer.

7. The method according to claim 3, wherein the immunity-inducing agent further comprises an immunoenhancer.

* * * * *